(12) United States Patent
Apodaca et al.

(10) Patent No.: US 7,071,191 B2
(45) Date of Patent: Jul. 4, 2006

(54) NON-IMIDAZOLE ARYLOXYPIPERIDINES

(75) Inventors: Richard Apodaca, San Diego, CA (US); Nicholas I. Carruthers, Poway, CA (US); Curt A. Dvorak, San Diego, CA (US); Chandravadan R. Shah, San Diego, CA (US); Wei Xiao, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 356 days.

(21) Appl. No.: 09/922,619

(22) Filed: Aug. 6, 2001

(65) Prior Publication Data

US 2002/0040024 A1 Apr. 4, 2002

Related U.S. Application Data

(60) Provisional application No. 60/223,768, filed on Aug. 8, 2000.

(51) Int. Cl.
*A61K 31/5375* (2006.01)
*C07D 413/12* (2006.01)

(52) U.S. Cl. .................... 514/237.2; 544/106; 544/129; 544/130; 544/360; 514/253.11

(58) Field of Classification Search ............ 514/253.11, 514/237.2; 544/130, 360
See application file for complete search history.

(56) References Cited

U.S. PATENT DOCUMENTS

| 5,182,291 | A | | 1/1993 | Gubin |
| 5,352,707 | A | | 10/1994 | Pompni |
| 5,580,883 | A | * | 12/1996 | Goto et al. |
| 5,883,096 | A | * | 3/1999 | Lowe et al. .................. 514/17 |
| 5,929,089 | A | | 7/1999 | Jegham et al. |

FOREIGN PATENT DOCUMENTS

| EP | 0 978 512 A1 | 2/2000 |
| EP | 0 982 300 A3 | 3/2000 |
| EP | 0 982 300 A2 | 3/2000 |
| WO | WO 93/20061 A1 | 10/1993 |
| WO | WO 95/14007 A1 | 5/1995 |
| WO | WO 97/17345 A1 | 5/1997 |
| WO | WO 99/42458 A1 | 8/1999 |
| WO | WO 00/06254 A2 | 2/2000 |

OTHER PUBLICATIONS

Greene Protective Groups in Organic Synthesis ((1981).*
PCT International Search Report PCT/US01/24660 dated Apr. 18, 2002.
Ganellin, C.R. et al.; "Synthesis of Potent Non–imidazole Histamine H3–Receptor Antagonists"; Arch. Pharm. Pharm. Med. Chem. (Weinheim, Ger.); 1998 331:395–404.
Meier, G. et al.; "Influence of imidazole replacement in different structural classes of histamine H3–receptor antagonists"; Eur. J. Pharm. Sci.; 2001 13:249–259.
Walczynski, K. et al, "Non–Imidazole Histamine H3 Ligands, Part 2: New 2–Substituted Benzothiazoles as Histamine H3 Antagonists"; Arch. Pharm. Pharm. Med. Chem. (Weinheim, Ger.); 1999 332:389–398.
Walczynski, K. et al. "Non–Imidazole Histamine H3 Ligands. Part I. Synthesis of 2–(1–piperazinyl)– and 2–(hexahydro–1H–1,4–diazepin–1–yl)benzothiazole Derivatives as H3–Antagonists with H1 Blocking Activities"; IL Farmaco; 1999 54:684–694.
Ganellin, C. Robin, et al.: "Synthesis of Potent Non–imidazole Histamine H3–Receptor antaonists"; Archiv Der Pharmazie., 1998, pp. 395–404, vol. 331, XP002123596 VCH Verlagsgesellschaft MGH, Weinhelm, DE ISSN; 0365–06233.
Stark, H., et al.: "General Construction Pattern of Histamine H3–Receptor Antaonists: Change of a paradigm" Bioorganic & Medicinal Chemistry Letters, 1998, pp. 2011–2016, No. 8, XP004137177 Oxford, GB ISSN: 0960–894X.

* cited by examiner

*Primary Examiner*—Golam M M Shameem
(74) *Attorney, Agent, or Firm*—John Harbour; Gabriel Lopez

(57) ABSTRACT

Substituted non-imidazole aryloxypiperidine compounds, compositions containing them, and methods of making and using them to treat or prevent histamine-mediated conditions.

17 Claims, No Drawings

NON-IMIDAZOLE ARYLOXYPIPERIDINES

This application claims the benefit of provisional application No. 60/223,768 filed Aug. 8, 2000.

FIELD OF THE INVENTION

The present invention relates to aryloxypiperidines, their synthesis and their use, for example, for the treatment of disorders and conditions mediated by the histamine receptor.

BACKGROUND OF THE INVENTION

Histamine [2-(imidazol-4-yl)ethylamine] is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., *Br. J. Pharmacol.*, 1966, 27, 427) and are blocked by the classical antihistamines (e.g. diphenhydramine). Histamine is also an important regulator of gastric acid secretion through its action on parietal cells. These effects of histamine are mediated via the $H_2$ receptor (Black, J. W., Duncan, W. A. M., Durant, C. J., Ganellin, C. R. and Parsons, E. M., *Nature*, 1972, 236, 385) and are blocked by $H_2$ receptor antagonists (e.g. cimetidine). The third histamine receptor —$H_3$— was first described as a presynaptic autoreceptor in the central nervous system (CNS) (Arrang, J.-M., Garbarg, M., and Schwartz, J.-C., *Nature* 1983, 302, 832) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: "*The Histamine $H_3$ Receptor-A Target for New Drugs*", Leurs, R., and Timmerman, H., (Editors), Elsevier, 1998; Morisset et al., *Nature*, 2000, 408, 860–864.) A fourth histamine receptor —$H_4$— was recently described by Oda et al., (J. Biol. Chem., 2000, 275, 36781–36786).

The potential use of histamine $H_3$ agonists in sleep/wake and arousal/vigilance disorders is suggested based on animal studies (Lin et al, *Br. Res.*, 1990, 523, 325; Monti et al *Eur. J. Pharmacol.*, 1991, 205, 283). Their use in the treatment of migraine has also been suggested (McLeod et al *Abstr. Society Neuroscience*, 1996, 22, 2010) based on their ability to inhibit neurogenic inflammation. Other applications could be a protective role in myocardial ischemia and hypertension where blockade of norepinephrine release is beneficial (Imamura et al *J. Pharmacol. Expt. Ther.*, 1994, 271, 1259). It has been suggested that histamine $H_3$ agonists may be beneficial in asthma due to their ability to reduce non-adrenergic non-cholinergic (NANC) neurotransmission in airways and to reduce microvascular leakage (Ichinose et al *Eur. J. Pharmacol.*, 1989,174, 49).

Several indications for histamine $H_3$ antagonists and inverse agonists have similarly been proposed based on animal pharmacology experiments with known histamine $H_3$ antagonists (e.g. thioperamide). These include dementia, Alzheimer's disease (Panula et al *Abstr. Society Neuroscience*, 1995, 21,1977), epilepsy (Yokoyama et al *Eur. J. Pharmacol.*, 1993, 234, 129) narcolepsy, eating disorders (Machidori et al *Brain Research* 1992, 590, 180), motion sickness, vertigo, attention deficit hyperactivity disorders (ADHD), learning and memory (Barnes et al *Abstr. Society Neuroscience*, 1993,19,1813), schizophrenia (Schlicker et al *Naunyn-Schmiedeberg's Arch. Pharmacol.*, 1996, 353, 290–294); (also see; Stark et al *Drugs Future*, 1996,21, 507 and Leurs et al *Progress in Drug Research*, 1995, 45, 107 and references cited therein). Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5, 1998; *Bioworld Today*, Mar. 2, 1999) for the treatment of CNS disorders.

As noted, the prior art related to histamine $H_3$ ligands has been comprehensively reviewed ("*The Histamine $H_3$ Receptor—A Target for New Drugs*", Leurs, R., and Timmerman, H., (Editors), Elsevier, 1998). Within this reference the medicinal chemistry of histamine $H_3$ agonists and antagonists was reviewed (see Krause et al and Phillips et al respectively). The importance of an imidazole moiety containing only a single substitution in the 4 position was noted together with the deleterious effects of additional substitution on activity. Particularly methylation of the imidazole ring at any of the remaining unsubstituted positions was reported to strongly decrease activity. Additional publications support the hypothesis that an imidazole function is essential for high affinity histamine $H_3$ receptor ligands (See, Ali et al *J. Med. Chem.*, 1999, 42, 903 and Stark et al, *Drugs Future*, 1996, 21, 507 and references cited therein). However many imidazole containing compounds are substrates for histamine methyl transferase, the major histamine metabolizing enzyme in humans, which leads to shortened half lives and lower bioavailability (See, Rouleau et al *J. Pharmacol. Exp. Ther.* 1997, 281, 1085). In addition, imidazole containing drugs, via their interaction with the cytochrome P450 monooxygenase system, can result in unfavorable biotransformations due to enzyme induction or enzyme inhibition. (Kapetanovic et al *Drug Metab. Dispos.* 1984,12, 560; Sheets et al *Drug Metab. Dispos.* 1984, 12, 603; Back, et al Br. *J. Pharmacol.* 1985, 85, 121; Lavrijsen et al *Biochem. Pharmacol.* 1986, 35,1867; *Drug Saf.*, 1998, 18, 83). The poor blood brain barrier penetration of earlier histamine $H_3$ receptor ligands may also be associated with the imidazole fragment (Ganellin et al *Arch. Pharm. (Weinheim, Ger.)* 1998, 331, 395).

More recently, several publications have described histamine $H_3$ ligands that do not contain an imidazole moiety. For example; Ganellin et al *Arch. Pharm. (Weinheim, Ger.)* 1998, 331, 395; Walczynski et al *Arch. Pharm. (Weinheim, Ger.)* 1999, 332, 389; Walczynski et al Farmaco 1999, 684; Linney et al *J. Med. Chem.* 2000, 2362; Tozer and Kalindjian *Exp. Opin. Ther. Patents* 2000, 10, 1045–1055; U.S. Pat. No. 5,352,707; PCT Application WO99/42458, Aug. 26, 1999; and European Patent Application 0978512, Feb. 9, 2000.

The compounds of the present invention do not contain the imidazole moiety, and its inherent liabilities, and maintain potency at the human $H_3$ receptor. Thus in the present invention receptor binding was determined using the human histamine $H_3$ receptor (See Lovenberg et al *Mol. Pharmacol.* 1999, 1107). Screening using the human receptor is particularly important for the identification of new therapies for the treatment of human disease. Conventional binding assays for example are determined using rat synaptosomes (Garbarg et al *J. Pharmacol. Exp. Ther.* 1992, 263, 304), rat cortical membranes (West et al *Mol. Pharmacol.*, 1990, 610), and guinea pig brain (Korte et al Biochem. *Biophys. Res. Commun.* 1990, 978). Only limited studies have been performed previously using human tissue but these allude to significant differences in the pharmacology of rodent and primate receptors (West et al *Eur. J. Pharmacol.* 1999, 233).

We now describe a series of aryloxypiperidines with the ability to modulate the activity of the histamine receptor, specifically the $H_3$ receptor, without the inherent problems associated with the presence of an imidazolyl moiety.

SUMMARY OF THE INVENTION

The present invention is directed to a compound of formula (I):

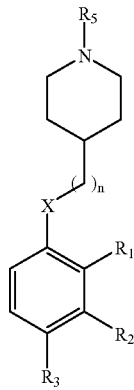

wherein
X is O;
n is an integer from 0 to 3;
$R_5$ is $C_{1-10}$ alkyl, $C_{3-8}$ alkenyl, $C_{3-8}$ cycloalkyl, $(C_{3-8}$ cycloalkyl) $C_{1-8}$ alkyl, (phenyl)$C_{1-6}$ alkyl, (phenyl)$C_{3-8}$ alkenyl, or $(C_{1-8}$ alkylcarbonyl)$C_{1-8}$ alkyl;
one of $R_1$, $R_2$, and $R_3$ is G or W, wherein one of the remaining two is selected from H and halogen, and the third being hydrogen;
G is a nitrogen-containing group selected from one of the following:

—OL$_1$Q, —L$_2$Q, —N(L$_1$Q)R$_5$, —L$_3$C(L$_1$Q)R$_6$R$_7$, —C(L$_1$Q)R$_6$R$_7$, (i)

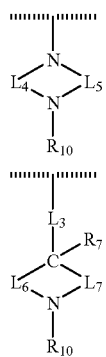

(ii)

(iii)

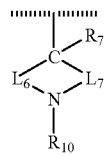

wherein:
$L_1$ is $C_{2-6}$ alkylene, $C_{3-8}$ cycloalkylene, $C_{4-6}$ alkenylene, $C_{4-6}$ alkynylene, $C_{2-5}$ alkanoyl, (phenyl)$C_{1-6}$ alkylene, (naphthyl)$C_{1-8}$ alkylene, $(C_{2-5}$ heteroaryl)$C_{1-6}$ alkylene, (phenoxy)$C_{1-6}$ alkylene, or $(C_{2-5}$ heteroaryloxy)$C_{1-6}$ alkylene;
$L_2$ is $C_{1-6}$ alkylene, $C_{3-8}$ cycloalkylene, $C_{3-6}$ alkenylene, $C_{3-6}$ alkynylene, $C_{2-5}$ alkanoyl, (phenyl)$C_{1-6}$ alkylene, (naphthyl)$C_{1-6}$ alkylene, $(C_{1-5}$ heteroaryl)$C_{1-6}$ alkylene, (phenoxy)$C_{1-6}$ alkylene, $(C_{1-5}$ heteroaryloxy) $C_{1-6}$ alkylene, or $(C_{1-5}$ heteroarylthio)$C_{1-6}$ alkylene;
$L_3$ is $C_{1-8}$ alkylene, $C_{2-6}$ alkenylene, $C_{2-6}$ alkynylene, $C_{2-5}$ alkanoyl, (phenyl)$C_{1-6}$ alkylene, phenyl, naphthyl, (naphthyl)$C_{1-8}$ alkylene, $C_{1-5}$ heteroaryl)$C_{1-6}$ alkylene, (phenoxy)$C_{1-6}$ alkylene, $(C_{1-5}$ heteroaryloxy)$C_{1-6}$ alkylene, or $C_{2-5}$ heteroaryl;
$L_4$ is $C_{1-5}$ alkylene;
$L_5$ is $C_{1-5}$ alkylene;
$L_6$ is $C_{1-5}$ alkylene;
$L_7$ is $C_{1-5}$ alkylene or absent;
Q is —NR$_8$R$_9$ or a non-aromatic $C_{2-15}$ heterocyclyl ring system containing at least one nitrogen atom and optionally between 1 and 3 additional heteroatoms selected from O, S, and N in each ring;
$R_6$ is independently selected from hydrogen, $C_{1-8}$ alkyl, $C_{1-6}$ alkoxy, $C_{2-8}$ alkenyl, $C_{3-7}$ cycloalkyl, $(C_{3-7}$ cycloalkyl)$C_{1-6}$ alkylene, $C_{2-15}$ heterocyclyl, and $(C_{2-7}$ heterocyclyl)$C_{1-6}$ alkylene;
$R_7$ is H, hydroxyl, halo, $C_{2-6}$ alkoxy or absent where the carbon linking $L_6$ and $L_7$ (or bonded to $R_6$) participates in a double bond;
each of $R_8$ and $R_9$ is independently selected from hydrogen, $C_{1-6}$ alkoxy, $C_{1-8}$ alkyl, $C_{3-8}$ alkenyl, $C_{3-7}$ cycloalkyl, $(C_{3-7}$ cycloalkyl)$C_{1-6}$ alkylene, $C_{2-15}$ heterocyclyl, phenyl, $(C_{2-15}$ heterocyclyl)$C_{1-6}$ alkylene, and (phenyl) $C_{1-6}$ alkylene;
$R_{10}$ is H, $C_{1-8}$ alkyl, $C_{3-8}$ alkenyl, $C_{3-7}$ cycloalkyl, $(C_{3-7}$ cycloalkyl)$C_{1-8}$ alkylene, $(C_{2-15}$ heterocyclyl)$C_{1-8}$ alkylene, or (phenyl) $C_{1-6}$ alkylene;
W is —CN, —CHO, halogen, $C_{1-8}$ heterocyclyl, $(C_{1-8}$ heterocyclyl)-O—, phenoxy, phenyl, (phenyl)$C_{1-6}$ alkylene-O—, —C(=O)$R_x$, —C(OH)$R_xR_y$, —$C_{1-8}$ alkyl, $C_{1-8}$ cycloalkyl, or —NR$_x$R$_y$;
wherein each of $R_x$ and $R_y$ is independently selected from H, $C_{1-6}$ alkyl, $C_{1-6}$ alkanoyl, $C_{1-8}$ heterocyclyl, and phenyl;
wherein each of the above alkyl, alkylene, alkenyl, alkenylene, alkynyl, alkynylene, heterocyclyl, cycloalkyl, and aryl groups may each be independently and optionally substituted with between 1 and 3 substituents selected from halo, amino, nitro, hydroxyl, and $C_{1-3}$ alkyl;
wherein substituents of Q can be further selected from carboxamide, $C_{2-6}$ alkyl, $C_{1-8}$ heterocyclyl, N($C_{1-6}$ alkyl)($C_{1-8}$ heterocyclyl), NH($C_{1-6}$ heterocyclyl), $(C_{1-3}$ alkylene)(C$_{1-8}$ heterocyclyl), O(C$_{1-8}$ heterocyclyl), O(C$_{1-6}$ alkyl), O(C$_{3-6}$ cycloalkyl), phenyl, (C$_{1-3}$ alkylene)phenyl, N(C$_{1-6}$ alkyl)(C$_{1-3}$ alkylene)phenyl, and O(C$_{1-3}$ alkylene)phenyl where each of above heterocyclyl, phenyl, and alkyl groups may be optionally substituted with from 1 to 3 substituents independently selected from halogen, nitro, cyano, and C$_{1-3}$ alkyl;

or a pharmaceutically acceptable salt, ester, or amide thereof.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or administering a combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine H$_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an H$_3$ antagonist and administering a jointly effective dose of a histamine H$_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion and allergic congestion.

In yet another embodiment, the disclosed compounds may be used in a combination therapy method, including administering a jointly effective dose of an H$_3$ antagonist and administering a jointly effective dose of a neurotransmitter re-uptake blocker, such as a selective serotonin re-uptake inhibitor (SSRI) or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia.

Additional features and advantages of the invention will become apparent from the detailed description and examples below, and the appended claims.

DETAILED DESCRIPTION OF THE INVENTION

The present invention provides aryloxypiperidine derivatives useful for the treatment of disorders and conditions modulated by a histamine receptor.

A. Terms

Certain terms are defined below and by their usage throughout this disclosure.

As used herein, "halogen" shall mean chlorine, bromine, fluorine and iodine, or monovalent radicals thereof.

As used herein, the term "alkyl", whether used alone or as part of a substituent group, shall include straight and branched carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1–4 carbon atoms. "Alkylene" refers to a bivalent hydrocarbyl group, such as methylene (CH$_2$), ethylene (—CH$_2$—CH$_2$—) or propylene (—CH$_2$CH$_2$CH$_2$—).

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohex-1,3-dienyl and the like.

As used herein, unless otherwise noted, "aryl" shall refer to carbocyclic aromatic groups such as phenyl, naphthyl, and the like. Divalent radicals include phenylene (—C$_6$H$_4$—) which is preferably phen-1,4-diyl, but may also be phen-1,3-diyl.

As used herein, unless otherwise noted, "aralkyl" shall mean any alkyl group substituted with an aryl group such as phenyl, naphthyl and the like. Examples of aralkyls include benzyl, phenethyl, and phenylpropyl.

As used herein, unless otherwise noted, the terms "heterocycle", "heterocyclyl" and "heterocyclo" shall denote any five-, six-, or seven-membered monocyclic, nine or ten membered bicyclic or thirteen or fourteen membered tricyclic ring structure containing at least one heteroatom moiety selected from the group consisting of N, O, SO, SO$_2$, (C=O), and S, and preferably N, O, or S, optionally containing one to four additional heteroatoms in each ring. In some embodiments, the heterocyclyl contains between 1 and 3 or between 1 and 2 additional heteroatoms. Unless otherwise specified, a heterocyclyl may be saturated, partially unsaturated, aromatic or partially aromatic. The heterocyclyl group may be attached at any heteroatom or carbon atom which results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl, tetrazolyl, azetidinyl and the like.

For example, where Q is a non-aromatic nitrogen-containing heterocyclyl, preferred values for Q include piperidyl, piperazinyl, pyrrolinyl, pyrrolidinyl, morpholinyl, and N-(C1–6 alkyl) piperazinyl. These may be linked to the rest of the molecule by a nitrogen or a carbon atom; in general, N-linked heterocyclyls are preferred. Q can be substituted with between 1 and 3 substituents selected from pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl. Examples of substituted Q, wherein the substituent comprises a heterocyclyl, include: 4-(4-chloropyridin-2-yl)amino-piperidin-1-yl; 4-(4-chloropyrimidin-2-yl)amino-piperidin-1-yl; 2-([1,2,4]triazol-1-yl)methyl-morpholin-1-yl; 3-(pyrazin-2-yl)piperidin-1-yl; 4-(pyrazol-1-yl)piperidin-1-yl; 4-(pyrimidin-2-yl)piperazin-1-yl; 4-(furan-2-yl)methylpiperazin-1-yl; 4-(thiophen-2-yl)methylpiperazin-1-yl; 4-(4-chloropyridin-2-yl)-[1,4]diazepan-1-yl; and 5-(isoxazol-5-yl)-2,5-diaza-bicyclo[2.2.1]heptan-2-yl.

Exemplary bicyclic heterocyclic groups include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b]pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl(such as 1,2,3,4-tetrahydroisoquiunolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

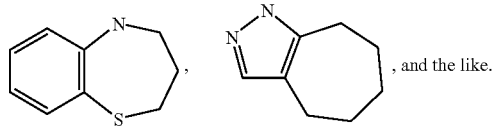
, and the like.

Exemplary tricyclic heterocylclic groups include acridinyl, phenoxazinyl, phenazinyl, phenothiazinyl, carbozolyl, perminidinyl, phenanthrolinyl, carbolinyl, naphthothienyl, thianthrenyl, and the like.

Preferred heterocyclyl groups include morpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7-tetrahydroindadolyl, benzoxazinyl, benzoaxzolyl, benzthiazolyl, benzimidazolyl, tetrazolyl, oxadiazolyl,

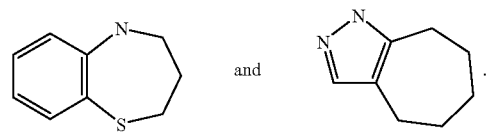

As used herein, unless otherwise noted, the term "heterocyclyl-alkyl" or "heterocyclyl-alkylene" shall denote any alkyl group substituted with a heterocyclyl group, wherein the heterocycly-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl (alkyl)amido(alkyl)" substituent refers to a group of the formula

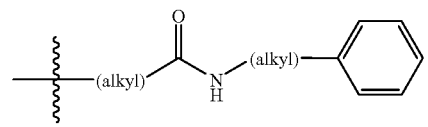

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly in the Schemes and Examples, are as follows:

| | |
|---|---|
| DBAD = | di-tert-butyl azodicarboxylate |
| DCE = | 1,2-dichloroethane |
| DCM = | dichloromethane |
| DEAD = | diethyl azodicarboxylate |
| DMA = | N,N-dimethylacetamide |
| DMAP = | 4-N,N-dimethylamino-pyridine |
| DME = | 1,2-dimethoxyethane |
| DMF = | dimethylformamide |
| DMSO = | dimethylsulfoxide |
| RT = | room temperature |
| TEA = | triethylamine |
| TFA = | trifluoroacetic acid |
| THF = | tetrahydrofuran |

The next section describes the compounds provided by the invention in more detail.

B. Compounds

The invention features compounds of formula (I) as described in the above Summary section and, for example, in the claims. Preferred compounds include those wherein:

(a) $R_5$ is $C_{1-5}$ alkyl, $C_{3-4}$ alkenyl, $C_{3-6}$ cycloalkyl, ($C_{3-6}$ cycloalkyl) $C_1$ alkylene, (phenyl)$C_{1-3}$ alkylene, or (phenyl)$C_{3-4}$ alkenylene;

(b) $R_5$ is branched $C_{3-5}$ alkyl, $C_{3-6}$ cycloalkyl, and ($C_{3-6}$ cycloalkyl )$C_1$ alkylene;

(c) one of $R_2$ and $R_3$ is G;

(d) $R_2$ is G;

(e) $R_3$ is G;

(f) $L_1$ is $C_{2-3}$ alkylene;

(g) $L_2$ is $C_{1-6}$ alkylene, ($C_{1-5}$ heteroaryl)$C_{1-6}$ alkylene, or -phenyl-$C_{1-6}$ alkylene;

(h) $L_2$ is methylene;

(i) $L_3$ is ethylene, vinylene, ethynylene, and phenylene;

(j) Q is a non-aromatic nitrogen-containing $C_{2-5}$ heterocyclyl;

(k) Q is selected from piperidyl, N—($C_{1-6}$ alkyl) piperazinyl, piperazinyl, pyrrolinyl, pyrrolidinyl, and morpholinyl;

(l) Q is N-morpholinyl or N-piperidinyl, optionally substituted with between 1 and 3 substituents selected from hydroxyl, carboxamide, $C_{1-6}$ alkyl, $C_{1-8}$ heterocyclyl, N($C_{1-6}$ alkyl)($C_{1-8}$ heterocyclyl), NH($C_{1-8}$ heterocyclyl), ($C_{1-3}$ alkylene)($C_{1-8}$ heterocyclyl), O($C_{1-8}$ heterocyclyl), O($C_{1-6}$ alkyl), O($C_{3-6}$ cycloalkyl), phenyl, ($C_{1-3}$ alkylene)phenyl, N($C_{1-6}$ alkyl)($C_{1-3}$ alkylene) phenyl, and O($C_{1-3}$ alkylene) phenyl where each of above heterocyclyl, phenyl, and alkyl groups may be optionally substituted with from 1 to 3 substituents independently selected from halogen, nitro, cyano, and $C_{1-3}$ alkyl;

(m) Q is substituted with a substituent comprising a $C_{1-6}$ heterocyclyl group selected from: pyridyl, pyrimidyl, furyl, thiofuryl, imidazolyl, ($C_{1-6}$ alkyl) imidazolyl, oxazolyl, thiazolyl, 2,3-dihydro-indolyl, benzimidazolyl, 2-oxobenzimidazolyl, ($C_{1-6}$ alkyl) tetrazolyl, tetrazolyl, ($C_{1-6}$ alkyl) triazolyl, triazolyl, ($C_{1-6}$ alkyl) pyrrolyl, and pyrrolyl;

(n) Q is a substituted or unsubstituted N-morpholinyl;

(o) Q is $NR_8R_9$ wherein each of $R_8$ or $R_9$ is independently selected from hydrogen, $C_{1-8}$ alkyl, $C_{3-8}$ alkenyl, $C_{3-7}$ cycloalkyl, ($C_{3-7}$ cycloalkyl)$C_{1-6}$ alkylene, $C_{2-5}$ heterocyclyl, phenyl, ($C_{2-5}$ heterocyclyl)$C_{1-6}$ alkylene, and (phenyl) $C_{1-6}$ alkylene;

(p) one of $R_8$ and $R_9$ is hydrogen;

(q) $R_8$ is H and $R_9$ is phenyl or aromatic $C_{1-8}$ heterocyclyl optionally substituted with 1–3 substituents selected from halo, nitro, cyano, and $C_{1-3}$ alkyl;

(r) $R_9$ is phenyl, pyridyl, pyrimidyl, furyl, thiofuryl, imidazolyl, ($C_{1-6}$ alkyl) imidazolyl, oxazolyl, thiazolyl, 2,3-dihydro-indolyl, benzimidazolyl, 2-oxobenzimidazolyl, ($C_{1-6}$ alkyl) tetrazolyl, tetrazolyl, ($C_{1-6}$ alkyl) triazolyl, triazolyl, ($C_{1-6}$ alkyl) pyrrolyl, and pyrrolyl;

(s) $R_5$ is $C_{1-5}$ alkyl, $C_{3-4}$ alkenyl, $C_{3-6}$ cycloalkyl, ($C_{3-6}$ cycloalkyl) $C_1$alkylene, (phenyl)$C_{1-3}$ alkylene, or (phenyl)$C_{3-4}$ alkenylene;

(t) n is 0 or 1;

(u) n is 0;

(v) G is selected from:
(1) formula (i) wherein $L_4$ and $L_5$ are independently selected from $C_{2-3}$ alkylene,
(2) formula (iii) wherein $L_8$ is $C_{2-3}$ alkylene and $L_7$ is $C_{2-3}$ alkylene or absent,
(3) $L_2Q$ wherein $L_2$ is $C_{1-6}$ alkylene, phenyl $C_{1-4}$ alkylene, or (aromatic $C_{1-5}$ heterocyclyl)$C_{1-4}$ alkylene, and
(4) $OL_1Q$ wherein $L_1$ is $C_{2-3}$ alkylene;

(w) G is selected from:
(1) formula (i) wherein $L_4$ and $L_5$ are each $C_2$ alkylene,
(2) formula (iii) wherein each of $L_6$ and $L_7$ is $C_2$ alkylene, and
(3) $L_2Q$ wherein $L_2$ is methylene;

(x) wherein G is $L_2Q$;

(y) $R_{10}$ is H, branched $C_{3-6}$ alkyl, or benzyl;

(z) $R_{10}$ is isopropyl or benzyl;

(aa) Q is a non-aromatic $C_{2-5}$ heterocyclyl;

(bb) Q is selected from piperidyl, N—($C_{1-6}$ alkyl) piperazinyl, piperazinyl, pyrrolinyl, pyrrolidinyl, and morpholinyl;

(cc) $R_5$ is $C_{1-5}$ alkyl, $C_{3-4}$ alkenyl, $C_{3-6}$ cycloalkyl, ($C_{3-6}$ cycloalkyl) $C_1$alkylene, (phenyl)$C_{1-3}$ alkylene, or (phenyl)$C_{3-4}$ alkenylene;

(dd) $R_7$ is hydroxyl, halo, or absent where one of $L_6$ and $L_7$ provides a double bond to the carbon atom to which $R_6$ and $R_7$ are attached;

(ee) one of $R_2$ and $R_3$ is G;

(ff) one of $R_2$ and $R_3$ is W, and W is a heterocyclyl selected from: pyridyl, pyrimidyl, furyl, thiofuryl, imidazolyl, oxazolyl, thiazolyl, 2,3-dihydro-indolyl, benzimidazolyl, tetrazolyl, triazolyl, and pyrrolyl;

(gg) $R_5$ is branched $C_{3-5}$ alkyl;

(hh) $R_5$ is isopropyl or cyclopentyl; or (ii) Combinations of the above.

Preferred compounds of the invention include: 4-(4-Imidazol-1-yl-phenoxy)-1-isopropyl-piperidine, 4-(4-Imidazol-1-yl-phenoxy)-1-isobutyl-piperidine, 1-Isopropyl-4-(4-pyrrol-1-yl-phenoxy)-piperidine, 5-Chloro-2-[4-(1-isopropyl-piperidin-4-yloxy)-phenyl]-1H-benzoimidazole, and more preferably, 4-(4-Imidazol-1-yl-phenoxy)-1-isopropyl-piperidine, 4-(4-Imidazol-1-yl-phenoxy)-1-isobutyl-piperidine, and 5-Chloro-2-[4-(1-isopropyl-piperidin-4-yloxy)-phenyl]-1H-benzoimidazole.

The invention also features: [4-(1-Isopropyl-piperidin-4-yloxy)-phenyl]-phenyl-methanone, 4-(Biphenyl-4-yloxy)-1-isopropyl-piperidine, 4-(4-Benzyloxy-phenoxy)-1- isopropyl-piperidine, 1-Isopropyl-4-(4-phenoxy-phenoxy)-piperidine, 4-(4-Benzyl-phenoxy)-1-isopropyl-piperidine, [4-(1-Isopropyl-piperidin-4-yloxy)-phenyl]-phenyl-methanol, N-[4-(1-Isopropyl-piperidin-4-yloxy)-phenyl]-acetamide, 4-(4-Cyclopentyl-phenoxy)-1-isopropyl-piperidine, 4-(1-Cyclopentyl-piperidin-4-yloxy)-benzonitrile, 4-(1-Cyclobutyl-piperidin-4-yloxy)-benzonitrile, 4-(1-sec-Butyl-piperidin-4-yloxy)-benzonitrile, 4-(1-Isopropyl-piperidin-4-yloxy)-benzaldehyde, 4-(1-Cyclohexyl-piperidin-4-yloxy)-benzonitrile, 4-(1-Isopropyl-piperidin-4-yloxy)-benzonitrile, 4-(1-Cyclopropylmethyl-piperidin-4-yloxy)-benzonitrile, 4-(1-Isobutyl-piperidin-4-yloxy)-benzonitrile, and 4-(1-Propyl-piperidin-4-yloxy)-benzonitrile.

The invention also provides more preferred compounds such as: 4-(Biphenyl-4-yloxy)-1-isopropyl-piperidine, 4-(4-Benzyloxy-phenoxy)-1-isopropyl-piperidine, 4-(4-Benzyl-phenoxy)-1-isopropyl-piperidine, 1-Isopropyl-4-(4-phenoxy-phenoxy)-piperidine, and N-[4-(1-Isopropyl-piperidin-4-yloxy)-phenyl]-acetamide.

Preferred compounds also include those such as: (A) 1-Isopropyl-4-[4-(1-isopropyl-piperidin-4-yloxy)-phenyl]-piperazine, and 1-[4-(1-Isopropyl-piperidin-4-yloxy)-phenyl]-piperazine 1-[4-(1-Isopropyl-piperidin-4-yloxy)-phenyl]-piperazine; and (B) 1-[4-(1-Isopropyl-piperidin-4-yloxy)-benzyl]-piperidine, 4-[4-(1-sec-Butyl-piperidin-4-yloxy)-benzyl]-morpholine, 1-[4-(1-Cyclopentyl-piperidin-4-yloxy)-benzyl]-piperidine, 1-[4-(1-Isobutyl-piperidin-4-yloxy)-benzyl]-piperidine, 1-N-Isopropyl-4-{4-[5-(1-isopropyl-piperidin-4-ylsulfanyl)-tetrazol-1-yl]-phenoxy}-piperidine, {1-[4-(1-Isopropyl-piperidin-4-yloxy)-benzyl]-piperidin-4-yl}-methanol, 1-[4-(1-Isopropyl-piperidin-4-yloxy)-benzyl]-4-methyl-[1,4]diazepane, 1-[4-(1-Isopropyl-piperidin-4-yloxy)-benzyl]-azepane, 1-[4-(1-Isobutyl-piperidin-4-yloxy)-benzyl]-piperidine, 1-[4-(1-Isopropyl-piperidin-4-yloxy)-benzyl]-piperidin-4-ol, [4-(1-Isopropyl-piperidin-4-yloxy)-benzyl]-methyl-(1-methyl-piperidin-4-yl)-amine, 1-[4-(1-isopropyl-piperidin-4-yloxy)-benzyl]-4-benzyl-piperidine, N-[4-(1-Isopropyl-piperidin-4-yloxy)-benzyl]-N,N',N'-trimethyl-ethane-1,2-diamine, 1-[4-(1-Isopropyl-piperidin-4-yloxy)-benzyl]-4-methyl-piperazine, Cyclohexyl-[4-(1-isopropyl-piperidin-4-yloxy)-benzyl]-methyl-amine, Butyl-[4-(1-isopropyl-piperidin-4-yloxy)-benzyl]-methyl-amine, 4-[4-(1-Cyclopentyl-piperidin-4-yloxy)-benzyl]-morpholine, 1-Isopropyl-4-(4-pyrrolidin-1-ylmethyl-phenoxy)-piperidine, Diethyl-[4-(1-isopropyl-piperidin-4-yloxy)-benzyl]-amine, 4-[4-(1-sec-Butyl-piperidin-4-yloxy)-benzyl]-morpholine, 1-[4-(1-isopropyl-piperidin-4-yloxy)-benzyl]-4-phenyl-piperazine, 1-Benzyl-4-[4-(1-isopropyl-piperidin-4-yloxy)-benzyl]-piperazine, 4-[4-(4-Benzylidene-piperidin-1-ylmethyl)-phenoxy]-1-isopropyl-piperidine, 4-[4-(1-Isopropyl-piperidin-4-yloxy)-benzyl]-morpholine, [4-(1-Isopropyl-piperidin-4-yloxy)-benzyl]-dimethyl-amine, 4-[4-(1-Cyclohexyl-piperidin-4-yloxy)-benzyl]-morpholine, 4-[4-(1-Isobutyl-piperidin-4-yloxy)-benzyl]-morpholine, 4-[4-(1-Propyl-piperidin-4-yloxy)-benzyl]-morpholine, 1-[4-(1-Cyclohexyl-piperidin-4-yloxy)-benzyl]-piperidine, 1-[4-(1-Benzyl-piperidin-4-yloxy)-benzyl]-piperidine, 1-[4-(1-Cyclohexylmethyl-piperidin-4-yloxy)-benzyl]-piperidine, and 4-[4-(4-Piperidin-1-ylmethyl-phenoxy)-piperidin-1-yl]-butan-2-one.

Highly preferred compounds include: 1-[4-(1-Isopropyl-piperidin-4-yloxy)-benzyl]-piperidine, 4-[4-(1-sec-Butyl-piperidin-4-yloxy)-benzyl]-morpholine, 1-[4-(1-Cyclopentyl-piperidin-4-yloxy)-benzyl]-piperidine, 1-[4-(1-Isobutyl-piperidin-4-yloxy)-benzyl]-piperidine, 1-N-Isopropyl-4-{4-[5-(1-isopropyl-piperidin-4-ylsulfanyl)-tetrazol-1-yl]-phenoxy}-piperidine, {1-[4-(1-Isopropyl-piperidin-4-yloxy)-benzyl]-piperidin-4-yl}-methanol, 1-[4-(1-Isopropyl-piperidin-4-yloxy)-benzyl]-4-methyl-[1,4] diazepane, 1-[4-(1-Isopropyl-piperidin-4-yloxy)-benzyl]-azepane, 1-[4-(1-Isobutyl-piperidin-4-yloxy)-benzyl]-piperidine, 1-[4-(1-Isopropyl-piperidin-4-yloxy)-benzyl]-piperidine, 1-[4-(1-Isopropyl-piperidin-4-yloxy)-benzyl]-piperidin-4-ol, [4-(1-Isopropyl-piperidin-4-yloxy)-benzyl]-methyl-(1-methyl-piperidin-4-yl)-amine, 1-[4-(1-isopropyl-piperidin-4-yloxy)-benzyl]-4-benzyl-piperidine, N-[4-(1-Isopropyl-piperidin-4-yloxy)-benzyl]-N,N',N'-trimethyl-ethane-1,2-diamine, 1-[4-(1-Isopropyl-piperidin-4-yloxy)-benzyl]-4-methyl-piperazine, Cyclohexyl-[4-(1-isopropyl-piperidin-4-yloxy)-benzyl]-methyl-amine, Butyl-[4-(1-isopropyl-piperidin-4-yloxy)-benzyl]-methyl-amine, 4-[4-(1-Cyclopentyl-piperidin-4-yloxy)-benzyl]-morpholine, 1-Isopropyl-4-(4-pyrrolidin-1-ylmethyl-phenoxy)-piperidine, Diethyl-[4-(1-isopropyl-piperidin-4-yloxy)-benzyl]-amine, 4-[4-(1-sec-Butyl-piperidin-4-yloxy)-benzyl]-morpholine, 1-[4-(1-Isopropyl-piperidin-4-yloxy)-benzyl]-4-phenyl-piperazine, 1-Benzyl-4-[4-(1-isopropyl-piperidin-4-yloxy)-benzyl]-piperazine, 4-[4-(4-Benzylidene-piperidin-1-ylmethyl)-phenoxy]-1-isopropyl-piperidine, 4-[4-(1-Isopropyl-piperidin-4-yloxy)-benzyl]-morpholine, [4-(1-Isopropyl-piperidin-4-yloxy)-benzyl]-dimethyl-amine, 4-[4-(1-Cyclohexyl-piperidin-4-yloxy)-benzyl]-morpholine, and 4-[4-(1-Isobutyl-piperidin-4-yloxy)-benzyl]-morpholine.

Examples of highly preferred compounds also include: Cyclopropyl-[4-(1-isopropyl-piperidin-4-yloxy)-benzyl]-amine, [4-(1-Isopropyl-piperidin-4-yloxy)-benzyl]-(5-methyl-pyridin-2-yl)-amine, [4-(1-Isopropyl-piperidin-4-yloxy)-benzyl]-pyridin-2-yl-amine, [4-(1-Isopropyl-piperidin-4-yloxy)-benzyl]-phenyl-amine, and (5-Chloro-pyridin-2-yl)-[4-(1-isopropyl-piperidin-4-yloxy)-benzyl]-amine.

The invention also provides compounds that are useful as synthetic intermediates of the compounds of the invention. Such compounds, which themselves may or may not have pharmaceutical activity, include those provided in the Schemes and synthetic examples.

The invention also contemplates compounds isotopically-labelled to be detectable by positron emission tomography (PET) or single-photon emission computed tomography (SPECT) useful for studying $H_3$-mediated disorders.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

HYDROXYL PROTECTING GROUPS

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

PROTECTION FOR 1,2- AND 1,3-DIOLS

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

AMINO PROTECTING GROUPS

Protection for the amino group includes carbamates, amides, and special—NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p- toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyidisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

SPECIAL—NH PROTECTIVE GROUPS

Examples of special NH protective groups include:

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-4-methoxybenzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl) imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Monoprotection of Dicarbonyl Compounds

Selective Protection Of α-and β-Diketones

Examples of selective protection of α-and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals

Examples of cyclic ketals, monothio and dithio ketals include bismethylenedioxy derivatives and tetramethylbis-methylenedioxy derivatives.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6- dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyidimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

The compounds of the invention can be prepared according to the methods described in the next section.

C. Synthesis

The compounds of the invention can be prepared according to traditional synthetic organic methods and matrix or combinatorial chemistry methods, as shown in Schemes 1–10 below and in Examples 1–86. A person of ordinary skill will be aware of variations and adaptations of the schemes and examples provided to achieve the compounds of the invention.

Throughout the schemes when the reacting functionality is located at $R_3$, one skilled in the art will recognize that the choice of $R_3$ is illustrative only and that the reacting functionality could also be located at $R_1$ and $R_2$ also.

Compounds of formula (I) may be prepared according to the processes outlined in Scheme 1.

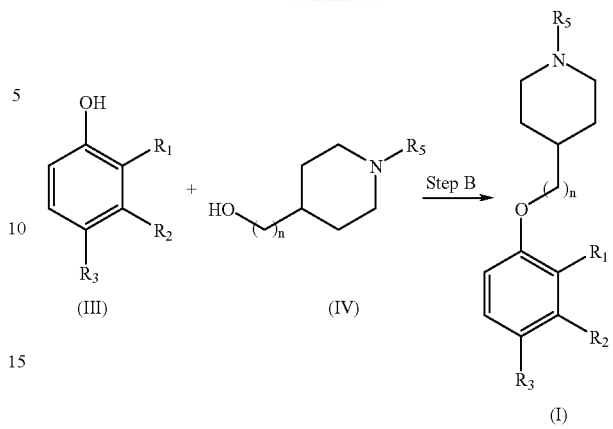

A compound of formula (I) is prepared as outlined in Scheme 1 by reacting a compound of formula (II) or a compound of formula (III) with a compound of formula (IV). A compound of formula (II) is reacted with a compound of formula (IV) in the presence of a base such as $Cs_2CO_3$, $K_2CO_3$, $Na_2CO_3$, NaOH, KOH, LDA, LHMDS, or the like, in a solvent, for example DMF, DMA, THF, DME, DCM, and DMSO at a temperature from ambient to about 200° C. In a preferred embodiment the base is selected from $Cs_2CO_3$, $K_2CO_3$, and $Na_2CO_3$ in a solvent selected from DMF, DMA. In a particularly preferred embodiment the base is $Cs_2CO_3$ and the solvent DMF at a temperature from 80 to 150° C. One skilled in the art will recognize that the compound of formula (II) should contain both an $X_1$ substituent which is a leaving group, and a $R_1$ or $R_3$ group which is electron-withdrawing in order that the reaction with a compound of formula (IV) proceed. Preferred $R_1$ and $R_3$ substituents include —$NO_2$, —CHO, —CN, $CO_2R_{15}$, $COR_{16}$, —$CONR_{17}R_{18}$, or the like. Preferred $X_1$ substituents include —F and —Cl, and —Br. Particularly preferred $R_1$ or $R_3$ substituents include —$NO_2$, —CHO, —CN, and $COR_{16}$. Particularly preferred $X_1$ substituents include —F and —Cl. A compound of formula (I) may be prepared by reacting a compound of formula (III) with a compound of formula (IV) according to the Mitsunobu procedure (in the presence of triphenylphosphine or polymer supported triphenyl phosphine and DBAD or DEAD, in an organic solvent such as DCM, THF, and the like), to yield the corresponding compound of formula (I).

A compound of formula (VI) is prepared from a compound of formula (V) as outlined in Scheme 2.

Scheme 1

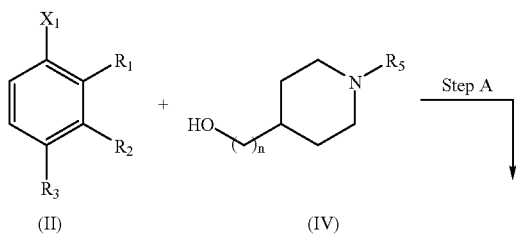 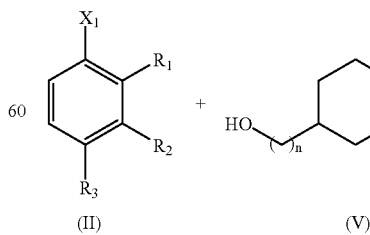

Scheme 2

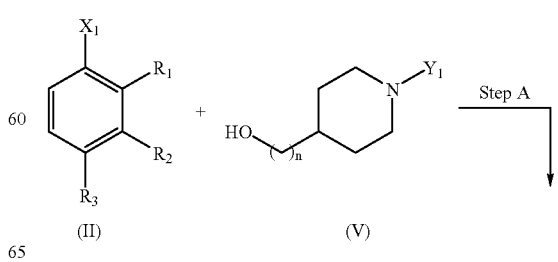

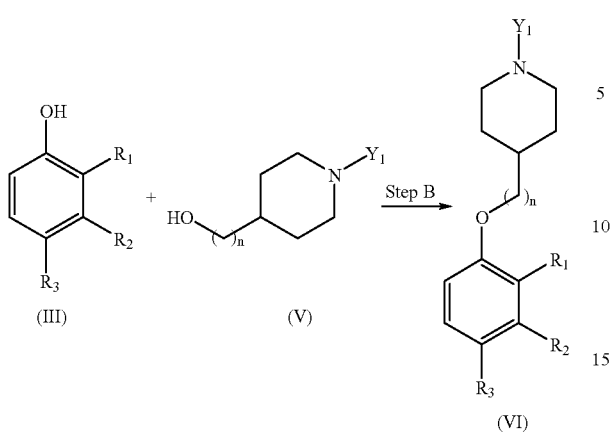

A compound of formula (VI) is prepared by reacting a compound of formula (V) with a compound of formula (II), or a compound of formula (III) according to the procedures of Step A and Step B of Scheme 1, respectively. The group $Y_1$ represents a protecting group. One skilled in the art will select the appropriate protecting group compatible with the desired reactions. Examples of preferred protecting groups include; carbamates, benzyl and substituted benzyl groups. Especially preferred protecting groups are; tert-butyloxycarbonyl, 2,2,2-trichloroethoxycarbonyl, alpha-chloroethoxycarbonyl, benzyl, 4-nitrobenzyl and diphenylmethyl.

A compound of formula (XI) is prepared from a compound of formula (VI) as outlined in Scheme 3.

Scheme 3

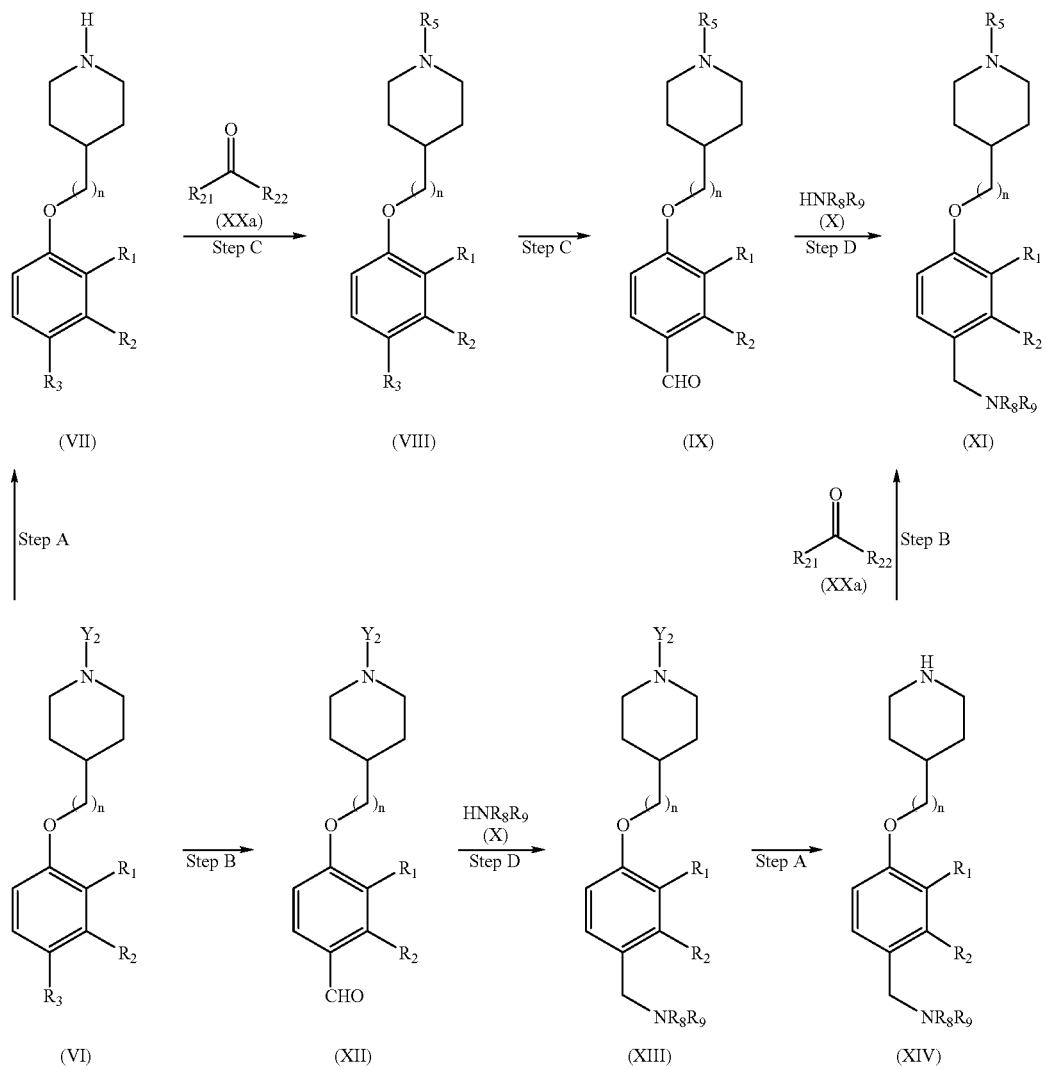

Thus in Step A, a compound of formula (VI) in which $Y_2$ is a nitrogen protecting group is reacted under the appropriate conditions to obtain a compound of formula (VII). In a preferred embodiment $Y_2$ is a benzyl or tert-butoxycarbonyl group which may be removed via hydrogenolysis or acidic hydrolysis respectively. In a more preferred embodiment the protecting group is tert-butoxycarbonyl and is removed with HCl in dioxane. A compound of formula (VIII) is obtained in Step B by reacting a compound of formula (VII) and a compound of formula (XXa) in the presence of a reducing agent such as sodium borohydride, sodium cyanoborohydride, sodium triacetoxyborohydride, or hydrogen gas or phenylsilane in the presence of a catalyst, and the like, in a solvent such as tetrahydrofuran, methanol, ethanol, 1,2-dichloroethane, trifluoroethanol, and the like, to yield the compound of formula (VIII). One skilled in the art will recognize that addition of acid to decrease the pH of the reaction mixture to a pH of less than about 7 may be necessary to effect reaction, wherein the acid is added as needed and is such as acetic acid, hydrochloric acid, and the like. Preferred reducing agents are sodium cyanoborohydride or sodium triacetoxyborohydride. A compound of formula (IX) is prepared from a compound of formula (VIII) in Step C by reacting a compound of formula (VIII), wherein $R_3$ is —CN, with a reducing agent. A preferred reducing agent is DIBAL in toluene at a temperature form $-78°$ C. to ambient temperature, preferably at $0°$ C. A compound of formula (XI) is prepared from a compound of formula (IX) in Step D, by reacting a compound of formula (IX) with a compound of formula (X) in the presence of a reducing agent such as sodium borohydride, sodium cyanoborohydride, sodium triacetoxyborohydride, hydrogen gas in the presence of a catalyst, and the like, in a solvent such as methanol, ethanol, 1,2-dichloroethane, trifluoroethanol, and the like. One skilled in the art will recognize that addition of acid to decrease the pH of the reaction mixture to a pH of less than about 7 may be necessary to effect reaction, wherein the acid is added as needed and is such as acetic acid, hydrochloric acid, and the like. One skilled in the art will furthermore recognize that a substituted or unsubstituted nonaromatic heterocycle containing secondary amine functionality may be used in place of the compound of formula (X). Preferred reducing agents are sodium cyanoborohydride or sodium triacetoxyborohydride. In an alternative embodiment a compound of formula (XI) is obtained from a compound of formula (VI). Thus a compound of formula (XII) is obtained from a compound of formula (VI) using the conditions of Step C. A compound of formula (XIII) is obtained from a compound of formula (XII) by reacting a compound of formula (XII) with a compound of formula (X) according to the conditions of Step D. A compound of formula (XIV) is obtained from a compound of formula (XIII) according to the conditions of Step A. A compound of formula (XI) is obtained from a compound of formula (XIV) by reacting a compound of formula (XIV) with a compound of formula (XXa) according to the procedure of Step B.

A compound of formula (XVI) is prepared from a compound of formula (IX), and a compound of formula (XVII) is prepared from a compound of formula (XII) as outlined in Scheme 4.

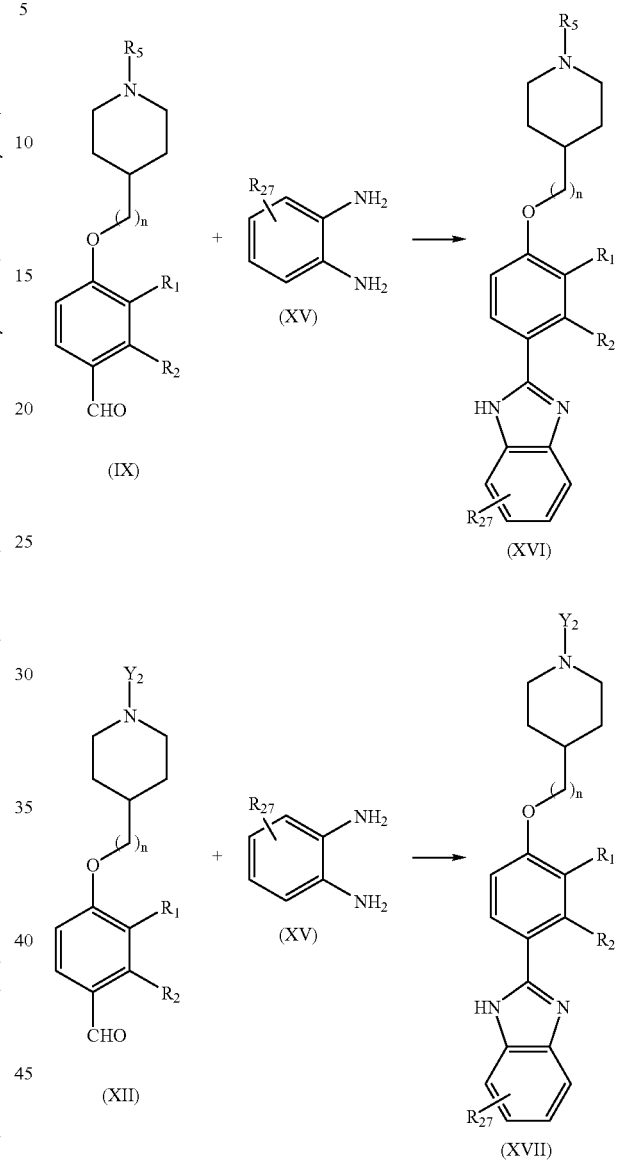

Scheme 4

A compound of formula (XVI) is prepared from a compound of formula (IX) by reacting a compound of formula (IX) with a compound of formula (XV). Thus a compound of formula (XVI) is reacted with a compound of formula (XV) in the presence of sodium metabisulfite in DMA at 80 to 120° C. to give a compound of formula (XVI). In a further embodiment a compound of formula (XII), wherein $Y_2$ is a protecting group, is reacted with a compound of formula (XV) under the same conditions to give a compound of formula (XVII).

A compound of formula (XXI), formula (XXIII) and formula (XIX) is prepared as outlined in Scheme 5.

Scheme 5

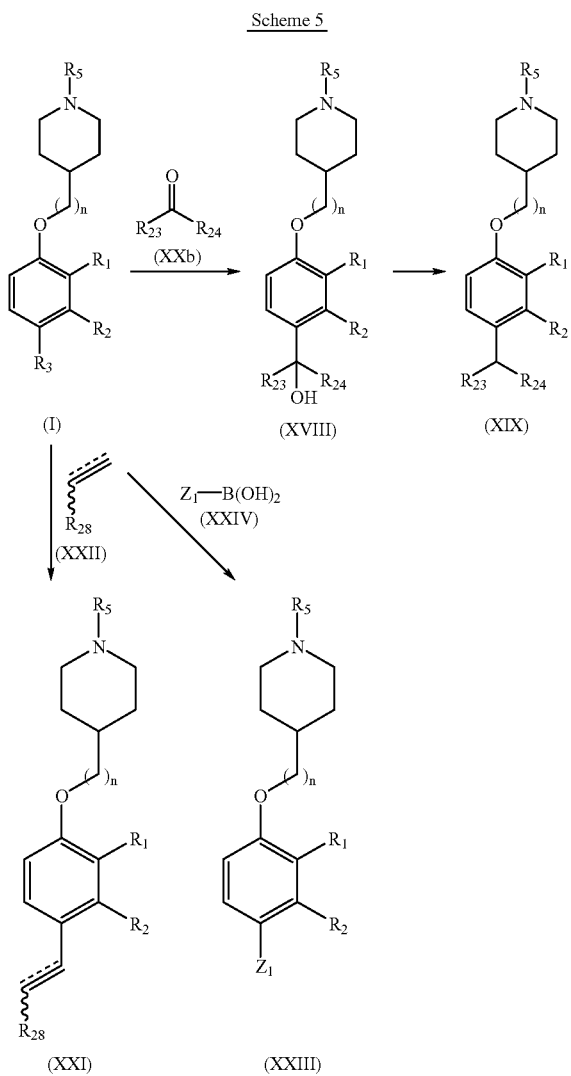

A compound of formula (XXI) is prepared from a compound of formula (I) in which $R_3$ is halogen by reacting a compound of formula (XXII) according to the Sonogashira coupling or Heck coupling procedures. In both cases the preferred halogen is Br and I with I being especially preferred. In a preferred embodiment a compound of formula (I) is reacted with a compound of formula (XXII) in the presence of a palladium catalyst and in the presence or absence of a copper catalyst. In a more preferred embodiment the catalyst is selected from; $Pd_2(dba)_3$, $PdCl_2$ and $Pd(OAc)_2$ with or without a phosphine additive. Preferred additives are triphenylphosphine and tri-(tert-butyl) phosphine. When the compound of formula (XXII) contains a triple bond (that is, when XXII is a terminal acetylene) an additional copper catalyst may be desirable. A preferred catalyst is a Cu(I) halide with CuI being especially preferred. A further preferred embodiment includes catalysts, together with a base selected from an amine, $Na_2CO_3$, $K_2CO_3$, or the like. A particularly preferred base is aqueous $K_2CO_3$. These reactions are carried out in a solvent selected from, THF, DMF, DME, DMA, benzene, toluene, DCM, or the like. Preferred solvents are THF and DME at from ambient temperature to the boiling point of the solvent. A compound of formula (XXIII) is prepared from a compound of formula (I) by reacting a compound of formula (I) where $R_3$ is halogen, preferably I, with a compound of formula (XXIV), according to the Suzuki procedure, in the presence of a catalyst such as tetrakis(triphenylphosphine) palladium (0), and the like, in the presence of a base such as sodium carbonate, potassium carbonate. A compound of formula (XIX) is prepared from a compound of formula (I). Thus a compound of formula (I), in which $R_3$ is halogen, preferably Br and I, is reacted with an organolithium reagent and subsequently with a compound of formula (XXb), in a solvent to give a compound of formula (XVIII). In a preferred embodiment the organolithium reagent is n-BuLi in THF at a temperature from −100 to 0° C., preferably at −78° C. A compound of formula (XIX) is prepared from a compound of formula (XVIII) by reacting a compound of formula (XVIII) with a reducing agent, such as sodium borohydride, or sodium cyanoborohydride in the presence of an acid such as HCl, AcOH, TFA, or the like, in a solvent such as THF and ether. In an alternative embodiment the compound of formula (XVIII) may be reacted with either hydrogen in the presence of a catalyst such as palladium on carbon, or triethylsilane in the presence of TFA. In preferred embodiment a compound of formula (XVIII) is reacted with triethylsilane in DCM at ambient temperature in the presence of TFA.

A compound of formula (XXV) is prepared from a compound of formula (XXIV) according to the procedure outlined in Scheme 6.

Scheme 6

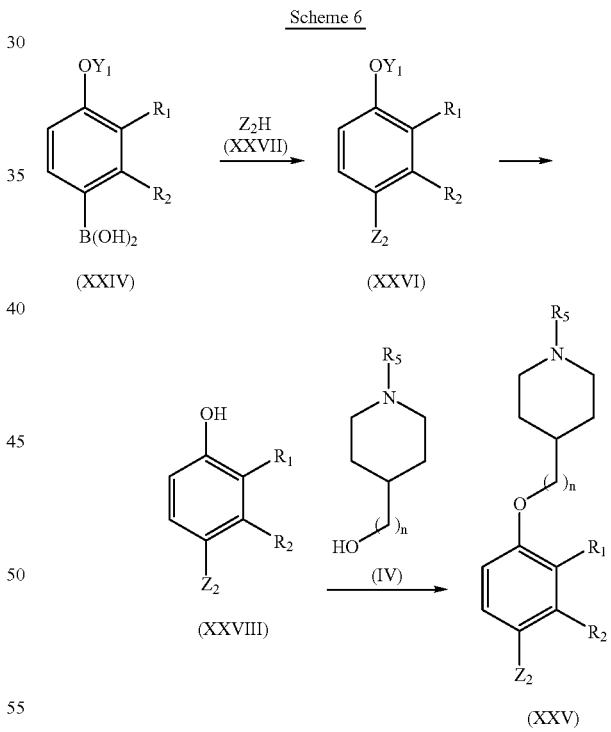

A compound of formula (XXIV), where $Y_1$ represents an oxygen protecting group, is reacted with a compound of formula (XXVII), where $Z_2H$ represents a heterocycle in which a nitrogen-hydrogen bond is present, to give a compound of formula (XXVI) where the group $Z_2$ is attached via a nitrogen atom. In a preferred embodiment a compound of formula (XXIV) is reacted with a compound of formula (XXVII) in the presence of $Cu(OAc)_2$, in the presence of a base such as pyridine, a dehydrating agent such as molecular sieves 4A in DCM at ambient temperature to give a compound of formula (XXVI). Removal of the protecting group $Y_1$ is accomplished under the appropriate conditions to give a compound of formula (XXVIII). One skilled in the art would be capable of selecting an appropriate protecting group. In one embodiment $Y_1$ is a substituted benzyl ether, which may be removed upon treatment with hydrogen in the presence of palladium on carbon. A compound of formula (XXV) is obtained by reacting a compound of formula (XXVIII) with a compound of formula (IV) according to the procedures outlined in Step B of Scheme 1.

A compound of formula (XXX) is obtained from a compound of formula (XXIX) as outlined in Scheme 7.

pyridine. When $X_2$ is OH a compound of formula (XXXI) is reacted with a compound of formula (XXXIII) via peptide coupling, for example in the presence of DCC in a solvent such as DCM or THF. A compound of formula (XXX) is prepared from a compound of formula (XXXII) using a reducing agent. Reducing agents include; $BH_3:THF$, and $BH_3:Me_2S$. A preferred reducing agent is $BH_3:Me_2S$, in THF at elevated temperature, preferably at the boiling point of the solvent.

A compound of formula (XXXV) may be prepared according to the processes outlined in Scheme 8.

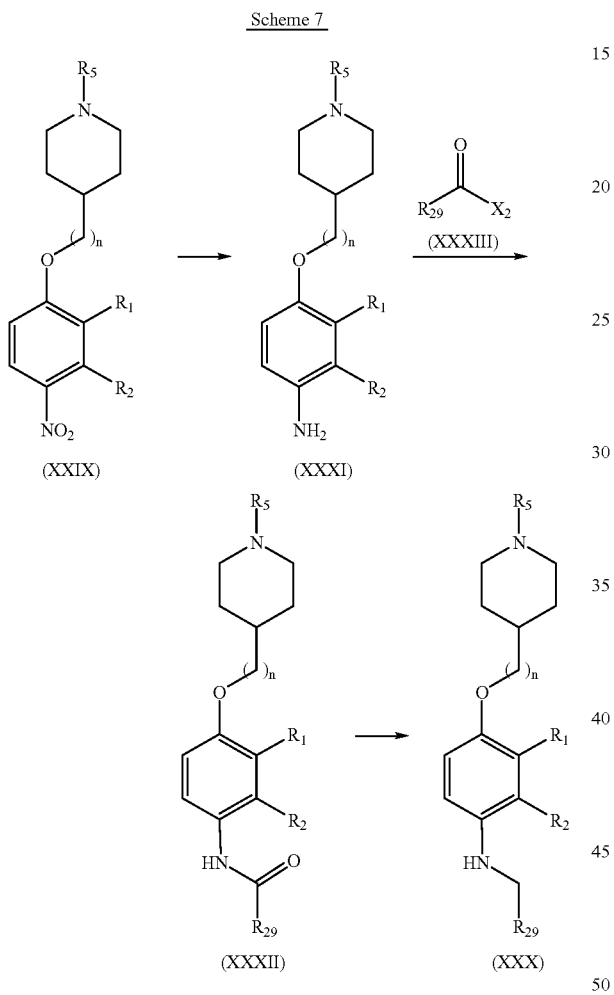

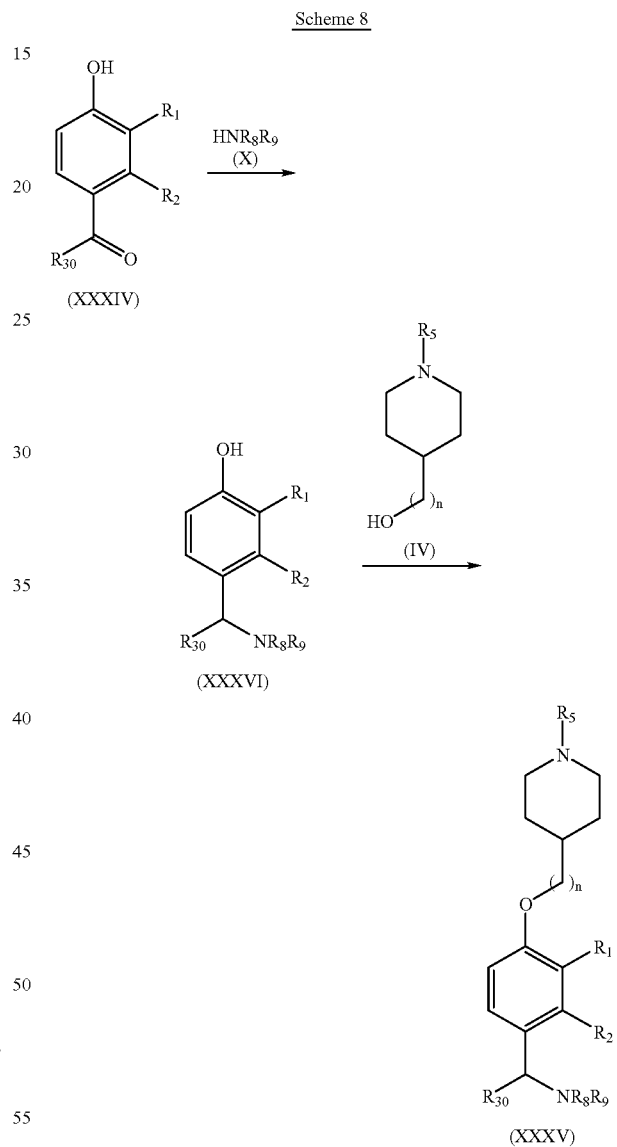

A compound of formula (XXXI) is obtained from a compound of formula (XXIX) by reacting a compound of formula (XXIX) with a reducing agent in a solvent. Reducing agents include hydrogen gas over a catalyst, for example palladium, platinum, Raney nickel or the like. In a preferred embodiment the reducing agent is $SnCl_2$ in ethanol in the presence or absence of water at ambient temperature to the boiling point of the solvent. A compound of formula (XXXII) is prepared from a compound of formula (XXXI) by reacting a compound of formula (XXXI) with a compound of formula (XXXIII) in which $X_2$ is a leaving group. In a preferred embodiment $X_2$ is Cl and OH. Thus when $X_2$ is Cl the compound of formula (XXXI) is reacted with a compound of formula (XXXIII) in a solvent such as DCM or THF in the presence of a base such as triethylamine or A compound of formula (XXXIV) is reacted with a compound of formula (X) in the presence of a reducing agent such as sodium borohydride, sodium cyanoborohydride, sodium triacetoxyborohydride, hydrogen gas in the presence of a catalyst, and the like, in a solvent such as methanol, ethanol, 1,2-dichloroethane, trifluoroethanol, and the like, to yield the compound of formula (XXXVI). One skilled in the art will recognize that addition of acid to decrease the pH of the reaction mixture to a pH of less than about 7 may be necessary to effect reaction, wherein the acid is added as needed and is such as acetic acid, hydrochloric acid, and the like. One skilled in the art will furthermore recognize that a substituted or unsubstituted nonaromatic heterocycle containing secondary amine functionality may be used in place of the compound of formula (X). A compound of formula (XXXVI) is reacted with a compound of formula (IV) according to the procedure of Step B, Scheme 1, to give a compound of formula (XXXV).

Compounds of formula (XXXVIII) may be prepared according to the processes outlined in Scheme 9.

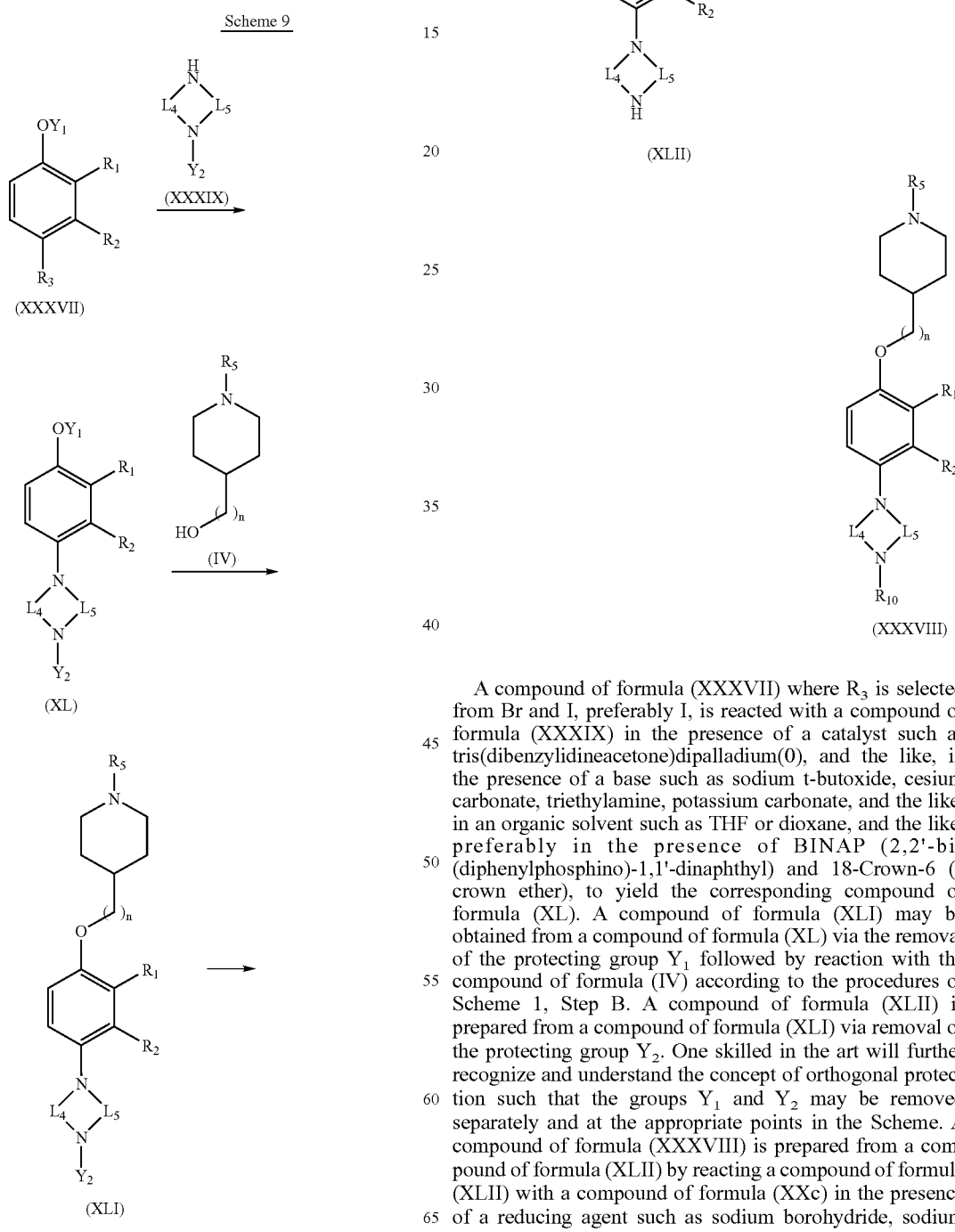

A compound of formula (XXXVII) where $R_3$ is selected from Br and I, preferably I, is reacted with a compound of formula (XXXIX) in the presence of a catalyst such as tris(dibenzylidineacetone)dipalladium(0), and the like, in the presence of a base such as sodium t-butoxide, cesium carbonate, triethylamine, potassium carbonate, and the like, in an organic solvent such as THF or dioxane, and the like, preferably in the presence of BINAP (2,2'-bis(diphenylphosphino)-1,1'-dinaphthyl) and 18-Crown-6 (a crown ether), to yield the corresponding compound of formula (XL). A compound of formula (XLI) may be obtained from a compound of formula (XL) via the removal of the protecting group $Y_1$ followed by reaction with the compound of formula (IV) according to the procedures of Scheme 1, Step B. A compound of formula (XLII) is prepared from a compound of formula (XLI) via removal of the protecting group $Y_2$. One skilled in the art will further recognize and understand the concept of orthogonal protection such that the groups $Y_1$ and $Y_2$ may be removed separately and at the appropriate points in the Scheme. A compound of formula (XXXVIII) is prepared from a compound of formula (XLII) by reacting a compound of formula (XLII) with a compound of formula (XXc) in the presence of a reducing agent such as sodium borohydride, sodium cyanoborohydride, sodium triacetoxyborohydride, hydrogen gas in the presence of a catalyst, and the like, in a solvent such as methanol, ethanol, 1,2-dichloroethane, trifluoroethanol, and the like, to yield the compound of formula (XXXVII). One skilled in the art will recognize that addition of acid to decrease the pH of the reaction mixture to a pH of less than about 7 may be necessary to effect reaction, wherein the acid is added as needed and is such as acetic acid, hydrochloric acid, and the like.

A compound of formula (XLIV) is prepared from a compound of formula (XLIII) according to the procedure outlined in Scheme 10.

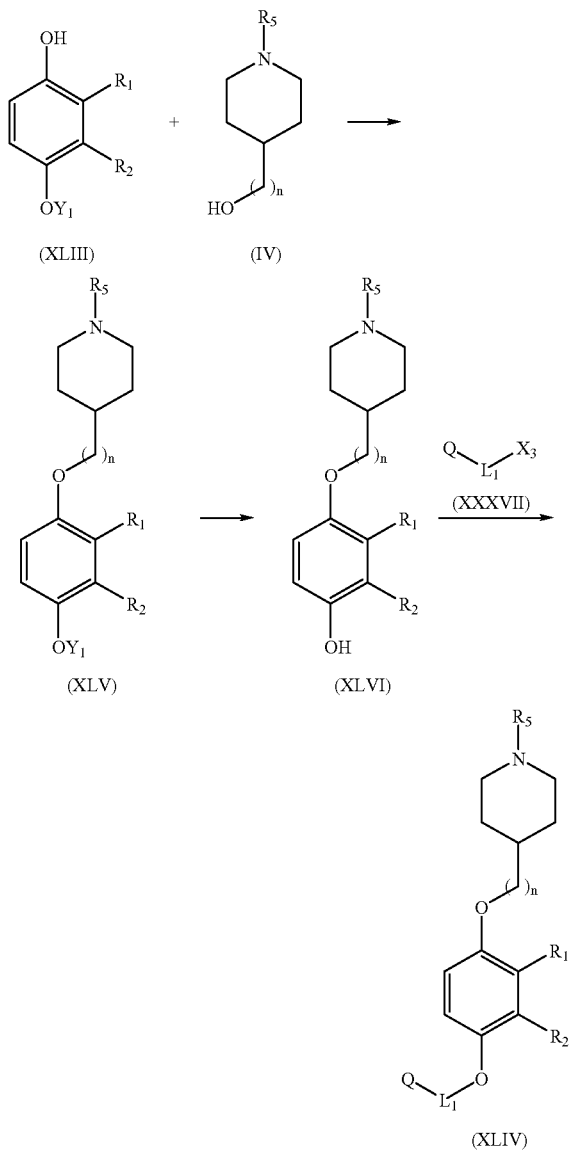

Compounds of formula (XLIII) are reacted with compounds of formula (IV) according to the procedure of Step B, Scheme 1 to give compounds of formula (XLV). Removal of the protecting group $Y_1$ affords compound of formula (XLVI). In a preferred embodiment the group $Y_1$ is a benzyl group, thus the compound of formula (XLV) is reacted with hydrogen or ammonium formate in the presence of a catalyst such as palladium on carbon, or the like, in a solvent such as methanol, ethanol and the like (i.e. catalytic hydrogenolysis) to yield the corresponding compound of formula (XLVI). The compound of formula (XLVI) is reacted with a compound of formula (XXXVII) where $X_3$ is selected from the group consisting Cl, Br, I, tosylate, mesylate, and the like, in the presence of a base such as sodium hydroxide, TEA, sodium hydride, potassium carbonate, and the like, in an organic solvent such as DCM, THF, DMF, DMA, and the like, to yield the corresponding compound of formula (XLIV). In an alternative embodiment the compound of formula (XXXVII) where $X_3$ is OH is reacted with a compound of formula (XLVI) according to the procedures of Step B, Scheme 1.

D. Formulation, Administration, and Therapy

The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof.

1. Formulation and Administration

The compounds or compositions of the invention may be formulated and administered to a subject by any conventional route of administration, including, but not limited to, intravenous, oral, subcutaneous, intramuscular, intradermal and parenteral administration. The quantity of the compound which is effective for treating each condition may vary, and can be determined by one of ordinary skill in the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali ml salts, e.g., sodium or potassium salts; alkaline earth ml salts, e.g., calcium or magnesium salts; and salts formed with suitable organic ligands, e.g., quaternary ammonium salts.

Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preption of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention also provides pharmaceutical compositions comprising one or more compounds of this invention in association with a pharmaceutically acceptable carrier and optionally additional pharmaceutical agents such as $H_1$ antagonists or SSRIs. Preferably these compositions are in unit dosage forms such as pills, tablets, caplets, capsules (each including immediate release, timed release and sustained release formulations), powders, granules, sterile parenteral solutions or suspensions (including syrups and emulsions), metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. Examples include 5 mg, 7 mg, 10 mg, 15 mg, 20 mg, 35 mg, 50 mg, 75 mg, 100 mg, 120 mg, 150 mg, and so on. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be septed by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compounds and compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrol idone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of ADHD is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

2. Combination Therapy

The disclosed compounds are useful in combination with other therapeutic agents, including $H_1$ receptor antagonists, $H_2$ receptor antagonists, and neurotransmitter modulators such as SSRIs and non-selective serotonin re-uptake inhibitors (NSSRIs).

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

E. Examples

Example 1

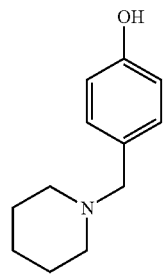

4-Piperidin-1-ylmethyl-phenol

A solution of 4-hydroxybenzaldehyde (10 g), piperidine (8.9 mL), and acetic acid (4.7 mL) in DCE (200 mL) was treated with sodium triacetoxyborohydride (24 g). After 16 h, the resulting mixture was treated with saturated aqueous sodium bicarbonate (100 mL) and extracted with DCM (5×100 mL). The combined organic phases were dried (magnesium sulfate) and evaporated. Trituration of the residue with ethyl acetate gave the title compound as a white crystalline solid (5.5 g).

Example 2

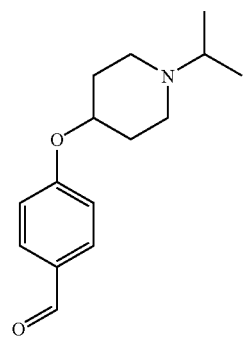

$K_i = 36$ nM 4-(1-Isopropyl-piperidin-4-yloxy)-benzaldehyde

A suspension of the product of Example 3 (5.7 g), 4-fluorobenzaldehyde (1.7 mL), and cesium carbonate (13 mg) in DMF (40 mL) was heated to 100° C. for 22 h, and allowed to cool to RT. Water (100 mL) was added, and the resulting mixture was extracted with ether (3×100 mL). The combined organic phases were dried (magnesium sulfate) and evaporated. Chromatography of the residue (0–15% 2M methanolic ammonia) gave the title compound as a colorless oil (2.0 g). $^1$H NMR (400 MHz, CDCl$_3$): 9.86 (s, 1H), 7.81 (d, J=8.6 Hz, 2H), 6.99 (d, J=8.6 Hz, 2H), 4.43 (m, 1H), 2.82–2.72 (m, 3H), 2.42 (m, 4H), 2.08–2.00 (m, 2H), 1.89–1.80 (m, 2H), 1.06 (d, J=6.6 Hz, 6H).

Example 3

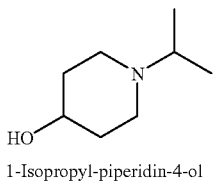

1-Isopropyl-piperidin-4-ol

A solution of 1-isopropyl-piperidin-4-one (51.2 g) in absolute ethanol (350 mL) was treated with sodium borohydride (7.30 g) at a rate not to exceed an internal temperature of 50° C. After 48 h, the solvent was evaporated and the resulting yellow paste was partitioned between DCM (300 mL) and 5% NaOH (300 mL). This mixture was stirred for 6 h and then extracted with DCM (4×100 mL). The combined organic phases were dried (sodium sulfate) and evaporated. Distillation of the yellow oil (bp 68° C., 1.5 mm Hg) gave the title compound as an off-white waxy solid (35.3 g).

Example 4

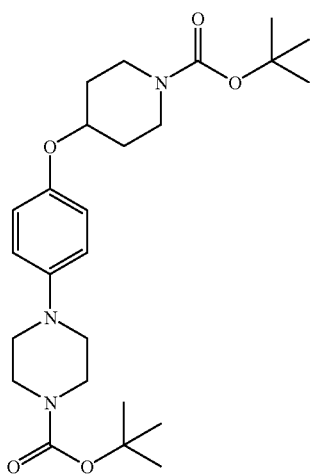

4-[4-(1-tert-Butoxycarbonyl-piperidin-4-yloxy)-phenyl]-piperazine-1-carboxylic acid tert-butyl ester A suspension of 4-(4-Hydroxy-phenyl)-piperazine-1-carboxylic acid tert-butyl ester (3.11 g), 4-Hydroxy-piperidine-1-carboxylic acid tert-butyl ester (3.51 g), and polymer supported triphenylphosphine (6.25 g; loading: 3 mmol/g) in DCM (100 mL) was treated with di-tert-butylazodicarboxylate (3.78 g). After 24 h, the resulting mixture was filtered, and the filtrate was evaporated. Chromatography of the residue (15–30% ethyl acetate/hexanes) gave the title compound as a white solid (3.20 g).

Example 5

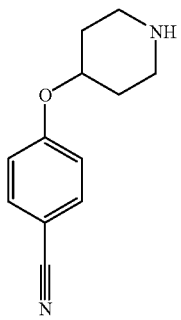

4-(Piperidin-4-yloxy)-benzonitrile

A solution of 4-hydroxy-piperidine-1-carboxylic acid tert-butyl ester (14.99 g) and 4-chlorobenzonitrile (10.35 g) in DMF (100 mL) was treated with sodium hydride (60%, 3.8 g). The resulting dark mixture was then heated to 65 C. for 16 h, and allowed to cool to RT. The mixture was poured into water (1 L) and extracted with ether (3×400 mL). The combined organic phases were evaporated and the brown oil dissolved in methanol (500 mL) and treated with concentrated hydrochloric acid (20 mL). After 24 h the methanol was removed, 5% aqueous sodium hydroxide (300 mL) and water (300 mL) were added, and the mixture was extracted with DCM (3×300 mL). The combined organic phases were dried (sodium sulfate) and evaporated. Bulb to bulb distillation of the residue gave the title compound as an off white waxy solid (12.23 g).

Example 6

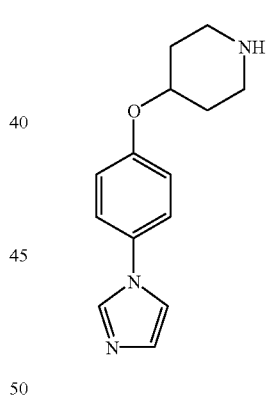

4-(4-Imidazol-1-yl-phenoxy)-piperidine

A solution of 4-hydroxy-piperidine-1-carboxylic acid tert-butyl ester (1.6 g), 4-imidazol-1-yl-phenol (1.2 g), and triphenylphosphine (2.4 g) in THF (10 mL) was treated with a solution of di-tert-butylazodicarboxylate (2.1 g) in THF (5 mL). After 24 h, the resulting mixture was evaporated. Chromatography of the residue (0–10% 2 M methanolic ammonia/DCM) gave a colorless glassy solid (1.9 g). This material was dissolved in methanol (10 mL) and treated with 2 M ethereal hydrogen chloride (14 mL). After 24 h, a white solid formed, which was filtered and washed with 1:1 methanol-ether and ether, yielding a white powder (1.2 g). To this material (1.1 g) was added 10% aqueous sodium hydroxide (20 mL) and DCM (20 mL). After 10 min vigorous stirring, the resulting mixture was extracted with DCM (2×15 mL). The combined organic phases were dried (magnesium sulfate) and evaporated, giving the title compound as a light pink solid (781 mg).

Example 7

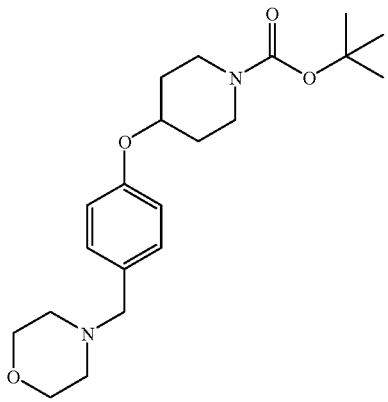

4-(4-Morpholin-4-ylmethyl-phenoxy)-piperidine-1-carboxylic acid tert-butyl ester A suspension of tert-butyl 4-hydroxy-1-piperidinecarboxylate (32.4 g), 4-flourobenzaldehyde (20.0 g), and cesium carbonate (52.5 g) in DMF (320 mL) was heated to 110 C for 48 h, and allowed to cool to RT. Water (400 mL) was added, and the resulting mixture was extracted with ether (3×500 mL). The combined organic phases were washed with water (3×200 mL), brine (200 mL), dried (magnesium sulfate) and evaporated. Toluene (2×200 mL) was added, and then evaporated, giving a brown-yellow oil (47.2 g). A solution of this oil (7.0 g), morpholine (2.4 mL), and acetic acid (1.3 mL) in DCM (300 mL) was treated with sodium triacetoxyborohydride (5.9 g). After 16 h, the resulting mixture was treated with 10% aqueous sodium hydroxide (50 mL), and extracted with DCM (2×500 mL). The combined organic phases were washed with water (100 mL), brine (100 mL), and then dried (magnesium sulfate) and evaporated. Chromatography of the residue (0.5 to 5.5% 2 M methanolic ammonia/DCM) gave the title compound as a yellow solid (6.6 g).

Example 8

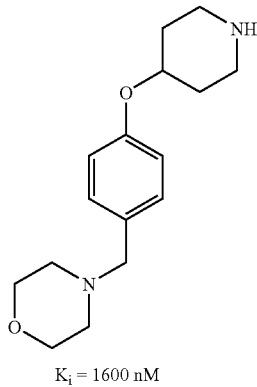

$K_i = 1600$ nM

4-[4-(Piperidin-4-yloxy)-benzyl]-morpholine

A solution of the product of Example 11 (6.6 g) in dioxane (40 mL) was treated with 4 N hydrogen chloride in dioxane (30 mL). The resulting mixture was stirred at RT for 16 h. Solvent was evaporated and the residue was treated with 10% aqueous sodium hydroxide (50 mL). The resulting mixture was extracted with DCM (2×500 mL). The combined organic phases were washed with water (200 mL), brine (200 mL), dried (magnesium sulfate), and evaporated to give the title compound as a yellow oil (5.4 g). $^1$H NMR (400 MHz, CDCl$_3$): 7.21 (d, J=8.6 Hz, 2H), 6.86 (d, J=8.6 Hz, 2H), 4.38–4.34 (m, 1H), 3.70 (t, J=4.6 Hz, 4H), 3.43 (s, 2H), 3.19–3.13 (m, 2H), 2.42 (t, J=4.3 Hz, 2H), 2.10–2.00 (m, 2H), 1.73–1.65 (m, 2H).

Example 9

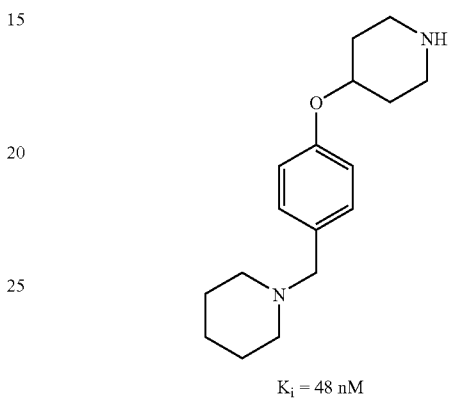

$K_i = 48$ nM

1-[4-(Piperidin-4-yloxy)-benzyl]-piperidine

A suspension of tert-butyl 4-hydroxy-1-piperidinecarboxylate (32.4 g), 4-fluorobenzaldehyde (20.0 g), and cesium carbonate (52.5 g) in DMF (320 mL) was heated to 110 C for 48 h and allowed to cool to RT. Water (400 mL) was added, and the resulting mixture was extracted with ether (3×500 mL). The combined organic phases were washed with water (3×200 mL), brine (200 mL), dried (magnesium sulfate) and evaporated. The residue was twice treated with toluene (2×200 mL) and evaporated, giving a brown-yellow oil (47.2 g). A solution of this oil (7.0 g), piperidine (2.8 mL), and acetic acid (1.3 mL) in DCM (300 mL) was treated with sodium triacetoxyborohydride (5.9 g). After 16 h, the resulting mixture was treated with 10% aqueous sodium hydroxide (50 mL), and extracted with DCM (2×500 mL). The combined organic phases were washed with water (100 mL), brine (100 mL), and then dried (magnesium sulfate) and evaporated. Chromatography of the residue (0.5 to 5.5% 2 M methanolic ammonia/DCM) gave the title compound as a yellow oil (8.6 g).

A solution of this oil (8.6 g) in dioxane (30 mL) was added 4 N hydrogen chloride in dioxane (40 mL). The resulting mixture was stirred at RT for 16 h and evaporated. The residue was treated with 10% aqueous sodium hydroxide (50 mL) and extracted with DCM (2×500 mL). The combined organic phases were washed with water (200 mL), brine (200 mL), dried (magnesium sulfate), and evaporated. Chromatography of the residue (0.5 to 5.5% 2 M methanolic ammonia/DCM) gave the title compound as an ivory solid (3.4 g). $^1$H NMR (400 MHz, CDCl$_3$): 7.20 (d, J=8.5Hz, 2H), 6.85 (d, J=8.6 Hz, 2H), 4.37–4.30 (m, 1H), 3.40 (s, 2H), 3.17–3.11 (m, 2H), 2.75–2.68 (m, 2H), 2.35 (br s, 4H), 2.03–1.99 (m, 2H), 1.69–1.61 (m, 2H), 1.59–1.53 (m, 2H), 1.43–1.39 (m, 2H).

Example 10

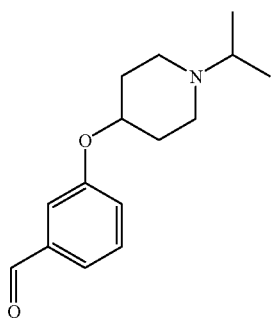

3-(1-Isopropyl-piperidin-4-yloxy)-benzaldehyde

A solution of the product of Example 3 (716 mg), 3-hydroxybenzaldehyde (672 mg), and triphenylphosphine (1.6 g) in THF (5 mL) was treated with a solution of di-tert-butylazodicarboxylate (1.4 g) in THF (5 mL). After 16 h, the resulting mixture was evaporated. The residue was treated with ether (20 mL) and 20% aqueous hydrochloric acid (20 mL). The aqueous phase was washed with ether (20 mL), neutralized with solid sodium carbonate, and extracted with ether (3×20 mL). The combined organic phases were dried (magnesium sulfate), and evaporated. Chromatography of the residue (0–10% 2M methanolic ammonia/DCM) gave the title compound as a colorless oil (50 mg).

Example 11

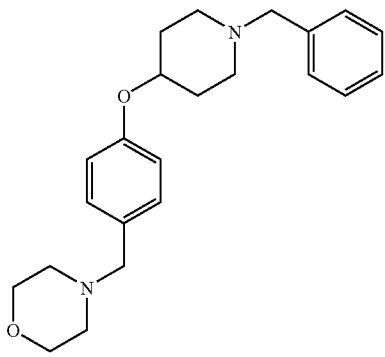

$K_i = 92$ nM

4-[4-(1-Benzyl-piperidin-4-yloxy)-benzyl]-morpholine

Phenylsilane (0.068 mL) was added dropwise to a solution of the product of Example 10 (137 mg), benzaldehyde (0.051 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a white solid (94 mg). $^1$H NMR (400 MHz, CDCl$_3$): 7.33–7.23 (m, 5H), 7.20 (d, J=8.6 Hz, 2H), 6.85 (d, J=8.6 Hz, 2H), 4.32–4.23 (m, 1H), 3.69 (t, J=4.6 Hz, 4H), 3.53 (s, 2H), 3.42 (s, 2H), 2.77–2.73 (m, 2H), 2.42 (t, J=4.3 Hz, 4H), 2.32–2.26 (m, 2H), 2.02–1.96 (m, 2H), 1.85–1.77 (m, 2H).

Example 12

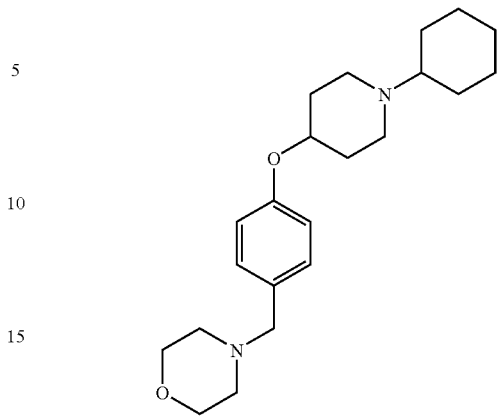

$K_i = 3.0$ nM

4-[4-(1-Cyclohexyl-piperidin-4-yloxy)-benzyl]-morpholine

Phenylsilane (0.068 mL) was added dropwise to a solution of the product of Example 10 (137 mg), cyclohexanone (0.052 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (73 mg). $^1$H NMR (400 MHz, CDCl$_3$): 7.21 (d, J=8.6 Hz, 2H), 6.85 (d, J=8.6 Hz, 2H), 4.33–4.29 (m, 1H), 3.70 (t, J=4.6 Hz, 4H), 3.42 (s, 2H), 2.92–2.86 (m, 2 H), 2.57–2.51 (m, 2H), 2.43–2.28 (m, 7 H), 2.09–2.02 (m, 2H), 1.92–1.81 (m, 6H), 1.31–1.20 (m, 4H).

Example 13

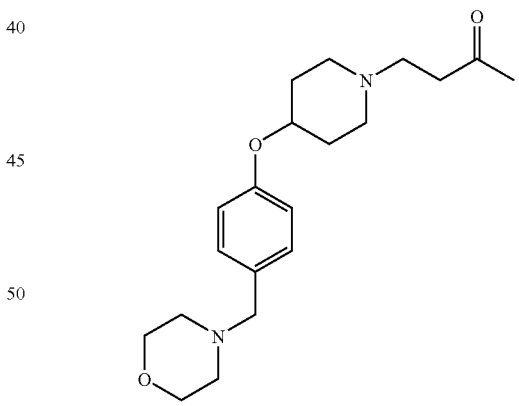

$K_i = 62$ nM

4-[4-(4-Morpholin-4-ylmethyl-phenoxy)-piperidin-1-yl]-butan-2-one

Phenylsilane (0.068 mL) was added dropwise to a solution of the product of Example 10 (137 mg), 4-hydroxy-2-butanone (44 mg) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (33 mg). $^1$H NMR (400 MHz, CDCl$_3$): 7.04 (d, J=8.5 Hz, 2H), 6.84 (d, J=8.6 Hz, 2H), 4.32–4.27 (m, 1H), 3.70 (t, J=4.6 Hz, 4 H), 3.42 (s, 2H), 2.74–2.62 (m, 4H), 2.43 (t, J=4.2 Hz, 4H), 2.33–2.27 (m, 2H), 2.18 (s, 3H), 2.02–1.76 (m, 6H).

Example 14

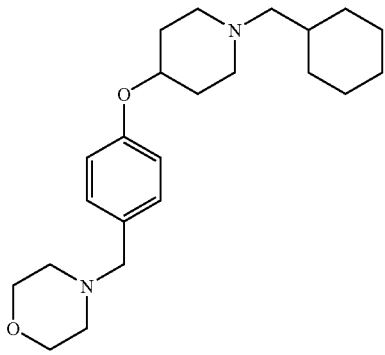

$K_i = 154$ nM

4-[4-(1-Cyclohexylmethyl-piperidin-4-yloxy)-benzyl]-morpholine

Phenylsilane (0.068 mL) was added dropwise to a solution of the product of Example 10 (137 mg), cyclohexanecarboxaldehyde (0.061 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (100 mg). $^1$H NMR (400 MHz, CDCl$_3$): 7.20 (d, J=8.6 Hz, 2H), 6.85 (d, J=8.6 Hz, 2H), 4.29–4.23 (m, 1H), 3.70 (t, J=4.6 Hz, 4H), 3.42 (s, 2H), 2.70 (t, J=4.6 Hz, 2H), 2.43 (t, J=4.2 Hz, 4H), 2.20 (t, J=9.1 Hz, 1H), 2.13 (d, J=7.1 Hz, 1H), 2.00–1.64 (m, 9H), 1.52–1.43 (m, 1H), 1.28–1.13 (m, 3H), 0.91–0.82 (m, 2H).

Example 15

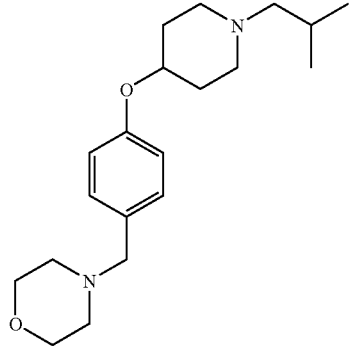

$K_i = 3.5$ nM

4-[4-(1-Isobutyl-piperidin-4-yloxy)-benzyl]-morpholine

Phenylsilane (0.068 mL) was added dropwise to a solution of the product of Example 10 (137 mg), isobutyraldehyde (0.091 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (198 mg). $^1$H NMR (400 MHz, CDCl$_3$): 7.20 (d, J=8.6 Hz, 2H), 6.85 (d, J=8.6 Hz, 2H), 4.29–4.23 (m, 1H), 3.70 (t, J=4.7 Hz, 4H), 3.42 (s, 2H), 2.72–2.69 (m, 2H), 2.42 (t, J=4.4 Hz, 4H), 2.19 (t, J=9.0 Hz, 1H), 2.09 (d, J=7.3 Hz, 1H), 2.00–1.95 (m, 2H), 1.83–1.72 (m, 3H), 0.90 (d, J=6.6 Hz, 6H).

Example 16

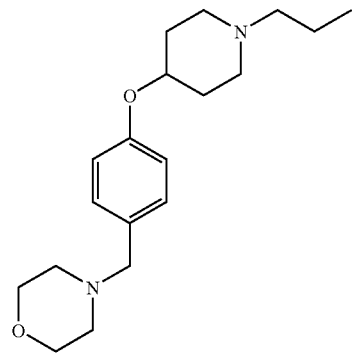

$K_i = 6.0$ nM

4-[4-(1-Propyl-piperidin-4-yloxy)-benzyl]-morpholine

Phenylsilane (0.068 mL) was added dropwise to a solution of the product of Example 10 (137 mg), propionaldehyde (0.072 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (85 mg). $^1$H NMR (400 MHz, CDCl$_3$): 7.21 (d, J=8.6 Hz, 2H), 6.85 (d, J=8.6 Hz, 2H), 4.34–4.28 (m, 1H), 3.70 (t, J=4.7 Hz, 4H), 3.42 (s, 2H), 2.79–2.75 (m, 2H), 2.42 (t, J=4.3 Hz, 4H), 2.37–2.33 (m, 4H), 2.06–1.99 (m, 2H), 1.88–1.80 (m, 2H), 1.59–1.50 (m, 2H), 0.91 (t, J=7.4 Hz, 6H).

Example 17

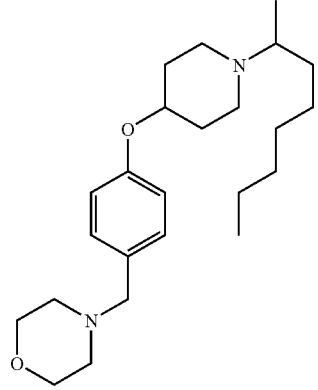

$K_i = 380$ nM

4-{4-[1-(1-Methyl-heptyl)-piperidin-4-yloxy]-benzyl}-morpholine

Phenylsilane (0.068 mL) was added dropwise to a solution of the product of Example 10 (137 mg), 2-octanone (0.156 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (108 mg). $^1$H NMR (400 MHz, CDCl$_3$): 7.20 (d, J=8.5 Hz, 2H), 6.85 (d, J=8.6 Hz, 2H), 4.29–4.24 (m, 1H), 3.70 (t, J=4.7 Hz, 4H), 3.42 (s, 2H), 2.80–2.73 (m, 2H), 2.60–2.57 (m, 1H), 2.48–2.33 (m, 6H), 1.99 (m, 2H), 1.84–1.74 (m, 1H), 1.57–1.54 (m, 9H), 0.94 (d, J=6.5 Hz, 3H), 0.90–0.87 (m, 3H).

Example 18

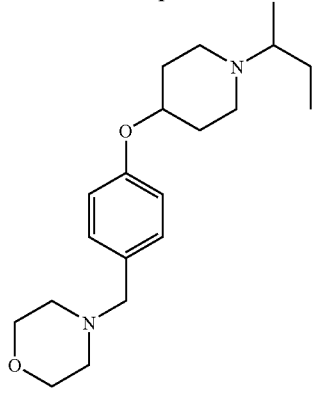

K$_i$ = 1.9 nM

4-[4-(1-sec-Butyl-piperidin-4-yloxy)-benzyl]-morpholine

Phenylsilane (0.068 mL) was added dropwise to a solution of the product of Example 10 (137 mg), 2-butanone (0.089 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (75 mg). $^1$H NMR (400 MHz, CDCl$_3$): 7.20 (d, J 8.6 Hz, 2H), 6.85 (d, J=8.6 Hz, 2H), 4.29–4.24 (m, 1H), 3.70 (t, J=4.7 Hz, 4H), 3.42 (s, 2H), 2.81–2.73 (m, 2H), 2.51–2.32 (m, 6H), 2.05–1.95 (m, 2H), 1.83–1.75 (m, 2H), 1.62–1.56 (m, 1H), 1.34–1.26 (m, 2H), 0.99 (d, J=6.6 Hz, 3H), 0.90 (t, J=7.4 Hz, 3H).

Example 19

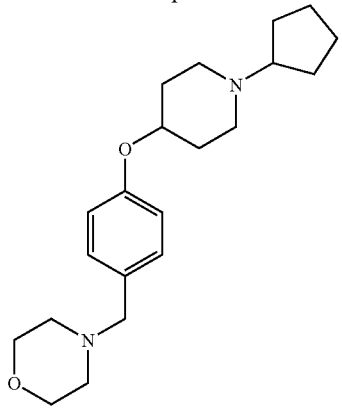

K$_i$ = 1.8 nM

4-[4-(1-Cyclopentyl-piperidin-4-yloxy)-benzyl]-morpholine

Phenylsilane (0.068 mL) was added dropwise to a solution of the product of Example 10 (137 mg), cyclopentanone (0.088 mL) and scandium trifluoromethanesulfonate (13 mg) in THF (1 mL). After 16 h, additional phenylsilane (0.036 mL) was added. After 4 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (168 mg). $^1$H NMR (400 MHz, CDCl$_3$): 7.22 (d, J=8.6 Hz, 2H), 6.85 (d, J=8.6 Hz, 2H), 4.44–4.35 (m, 1H), 3.70 (t, J=4.7 Hz, 4H), 3.43 (s, 2H), 2.95–2.88 (m, 1H), 2.76–2.54 (m, 2H), 2.42 (t, J 4.4 Hz, 4H), 2.16–2.08 (m, 2H), 1.94–1.91 (m, 4H), 1.78–1.72 (m, 2H), 1.62–1.57 (m, 4H).

Example 20

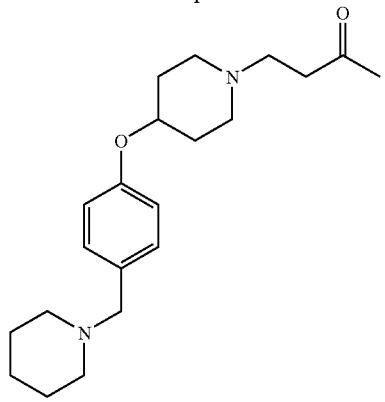

K$_i$ = 10 nM

4-[4-(4-Piperidin-1-ylmethyl-phenoxy)-piperidin-1-yl]-butan-2-one

Phenylsilane (0.068 mL) was added dropwise to a solution of the product of Example 9 (137 mg), 4-hydroxy-2-butanone (44 mg) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (42 mg). $^1$H NMR (400 MHz, CDCl$_3$): 7.19 (d, J=8.6 Hz, 2H), 6.83 (d, J=8.6 Hz, 2H), 4.31–4.26 (m, 1H), 3.40 (s, 2H), 2.75–2.61 (m, 4H), 2.36–2.22 (m, 6H), 2.18 (s, 3H), 2.27–1.72 (m, 6H), 1.59–1.53 (m, 4H), 1.47–1.35 (m, 2H).

Example 21

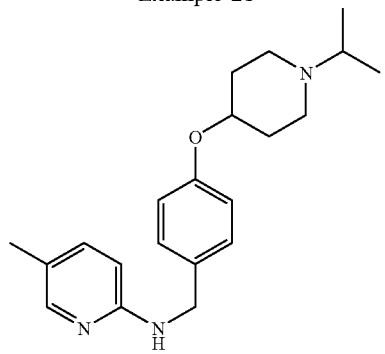

K$_i$ = 3.0 nM

[4-(1-Isopropyl-piperidin-4-yloxy)-benzyl]-(5-methyl-pyridin-2-yl)-amine

A solution of the product of Example 2 (175 mg), 2-amino-5-methylpyridine (87 mg), and acetic acid (0.05 mL) in DCE (3 mL) was treated with sodium triacetoxyborohydride (257 mg). After 16 h, the resulting mixture was treated with 10% sodium hydroxide (1 mL), and the mixture was extracted with DCM (3×3 mL). The combined organic phases were dried (magnesium sulfate) and evaporated. Chromatography of the residue (0–8% 2M methanolic ammonia/DCM) gave the title compound as a yellow waxy solid (103 mg). $^1$H NMR (400 MHz, CDCl$_3$): 7.93 (s, 1H), 7.26–7.21 (m, 3H), 6.86 (d, J=8.6 Hz, 2H), 6.32 (d, J=8.41, 1H), 4.66–4.61 (br m, 1 H), 4.39 (d, J=5.7, 2H), 4.31–4.24 (m, 1H), 2.81–2.70 (m, 3H), 2.42–2.34 (m, 2H), 2.17 (s, 3H), 2.04–1.96 (m, 2H), 1.86–1.76 (m, 2H), 1.07 (d, J=6.7, 6H).

Example 22

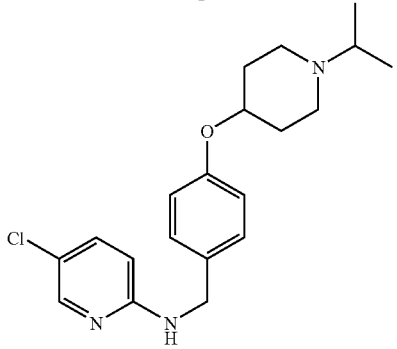

$K_i$ = 8.5 nM (5-Chloro-pyridin-2-yl)-[4-(1-isopropyl-piperidin-4-yloxy)-benzyl]-amine A solution of the product of Example 2 (200 mg), 2-amino-5-chloropyridine (104 mg), and acetic acid (0.05 mL) in DCE (3 mL) was treated with sodium triacetoxyborohydride (257 mg). After 16 h, the resulting mixture was treated with 10% sodium hydroxide (1 mL), and the mixture was extracted with DCM (3×3 mL). The combined organic phases were dried (magnesium sulfate) and evaporated. Chromatography of the residue (0–8% 2M methanolic ammonia/DCM) gave the title compound as a yellow amorphous solid (137 mg). $^1$H NMR (400 MHz, CDCl$_3$): 8.05 (s,1H), 7.35 (dd, J=8.8, 2.5 Hz, 1H), 7.24 (d, J=8.6 Hz, 2H), 6.87 (d, J=8.8 Hz, 2H), 6.32 (d, J=9.0 Hz, 1H), 4.84–4.78 (m, 1H), 4.39 (d, J=5.7 Hz, 2H), 4.31–4.25 (m, 1H), 2.81–2.70 (m, 3H), 2.41–2.35 (m, 2H), 2.05–1.96 (m, 2H), 1.84–1.76 (m, 2H), 1.05 (d, J=6.1 Hz, 6H).

Example 23

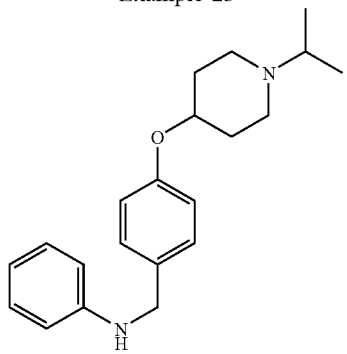

$K_i$ = 5.8 nM

[4-(1-Isopropyl-piperidin-4-yloxy)-benzyl]-phenyl-amine

A solution of the product of Example 2 (200 mg), aniline (104 mg), and acetic acid (0.05 mL) in DCE (3 mL) was treated with sodium triacetoxyborohydride (257 mg). After 16 h, the resulting mixture was treated with 10% sodium hydroxide (1 mL), and the mixture was extracted with DCM (3×3 mL). The combined organic phases were dried (magnesium sulfate) and evaporated. Chromatography of the residue (0–8% 2M methanolic ammonia/DCM) gave the title compound as a yellow amorphous solid (136 mg). $^1$H NMR (400 MHz, CDCl$_3$): 7.27 (d, J=8.2 Hz, 1H), 7.19–7.15 (m, 2H), 6.89 (d, J=8.6 Hz, 2H), 6.73–6.69 (m, 1H), 6.65–6.62 (m, 2H), 4.31–4.23 (m, 3H), 3.96–3.90 (br s,1H), 2.83–2.70 (m, 3H), 2.43–2.34 (m, 2H), 2.05–1.96 (m, 2H), 1.86–1.76 (m, 2H), 1.06 (d, J=6.7, 6H).

Example 24

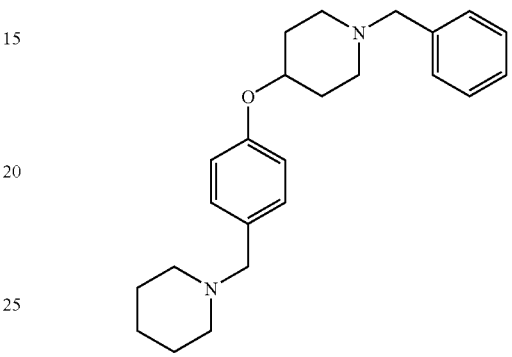

$K_i$ = 9.5 nM

1-[4-(1-Benzyl-piperidin-4-yloxy)-benzyl]-piperidine

Phenylsilane (0.068 mL) was added dropwise to a solution of the product of Example 9 (137 mg), benzaldehyde (0.051 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a white solid (145 mg). $^1$H NMR (400 MHz, CDCl$_3$): 7.34–7.23 (m, 5H), 7.21 (d, J=8.6 Hz, 2H), 6.85 (d, J=8.6 Hz, 2H), 4.32–4.26 (m, 1H), 3.53 (s, 2H), 3.48 (s, 2H), 2.90 (bs, 1H), 2.76–2.72 (m, 2H), 2.43 (bs, 3H), 2.39 (t, J=8.7 Hz, 2H), 2.01–1.96 (m, 2H), 1.85–1.77 (m, 2H), 1.63–1.57 (m, 4H), 1.47–1.38 (m, 2H).

Example 25

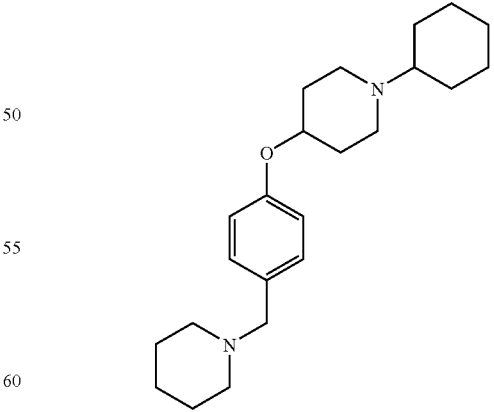

$K_i$ = 6.9 nM

1-[4-(1-Cyclohexyl-piperidin-4-yloxy)-benzyl]-piperidine

Phenylsilane (0.068 mL) was added dropwise to a solution of the product of Example 9 (137 mg), cyclohexanone (0.052 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (141 mg). $^1$H NMR (400 MHz, CDCl$_3$): 7.19 (d, J=8.6 Hz, 2H), 6.84 (d, J=8.6 Hz, 2H), 4.30–4.25 (m, 1H) 3.40 (s, 2H), 2.88–2.83 (m, 2H), 2.50–2.45 (m, 2H), 2.40–2.29 (m, 5H), 2.07–1.74 (m, 8H), 1.65–1.62 (m, 1H), 1.59–1.54 (m, 4H), 1.45–1.42 (m, 4H), 1.30–1.19 (m, 4H), 1.14–1.07 (m, 1H).

Example 26

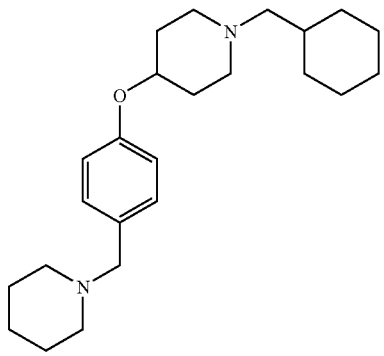

K$_i$ = 10 nM

1-[4-(1-Cyclohexylmethyl-piperidin-4-yloxy)-benzyl]-piperidine

Phenylsilane (0.068 mL) was added dropwise to a solution of the product of Example 9 (137 mg), cyclohexanecarbozaldehyde (0.061 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (163 mg). $^1$H NMR (400 MHz, CDCl$_3$): 7.19 (d, J=8.4 Hz, 2H), 6.84 (d, J=8.5 Hz, 2H), 4.27–4.23 (m, 1H), 3.40 (s, 2H), 2.76–2.64 (m, 2H), 2.43–2.28 (bs, 4H), 2.24–2.08 (m, 4H), 2.03–1.92 (m, 2H), 1.65–1.62 (m, 1H), 1.85–1.36 (m, 13H), 1.30–1.09 (m, 4H), 0.93–0.79 (m, 2H).

Example 27

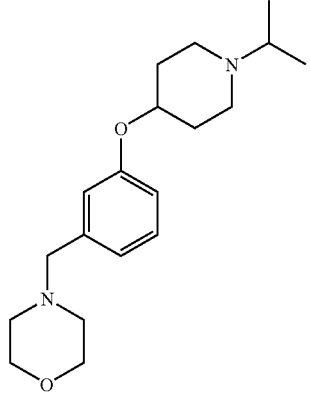

K$_i$ = 37 nM

4-[3-(1-Isopropyl-piperidin-4-yloxy)-benzyl]-morpholine

A solution of the product of Example 10 (50 mg) and morpholine (21 mg) in DCE (2 mL) was treated with sodium triacetoxyborohydride (64 mg). After 16 h, the resulting mixture was treated with 10% sodium hydroxide (1 mL), and the mixture was extracted with DCM (3×2 mL). The combined organic phases were dried (magnesium sulfate) and evaporated. Chromatography of the residue (0–15% 2M methanolic ammonia/DCM) gave the title compound as a colorless glassy oil (46 mg). $^1$H NMR (400 MHz, CDCl$_3$): 7.20 (t, J=7.6 Hz, 1H), 6.91–6.87 (m, 2H), 6.82–6.78 (m, 1H), 4.34–4.27 (m, 1H), 3.71 (t, J=3.71, 4H), 3.46 (s, 2H), 2.83–2.71 (m, 3H), 2.47–2.35 (m, 6H), 2.05–1.97 (m, 2H), 1.86–1.77 (m, 2H), 1.06 (d, J=6.5 Hz, 6H).

Example 28

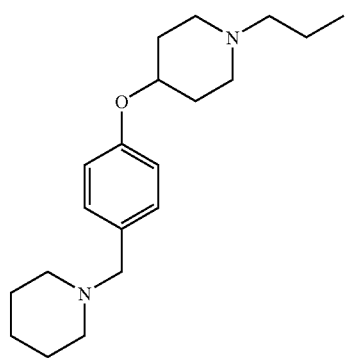

K$_i$ = 1.3 nM

1-[4-(1-Propyl-piperidin-4-yloxy)-benzyl]-piperidine

Phenylsilane (0.068 mL) was added dropwise to a solution of the product of Example 9 (137 mg), propionaldehyde (0.072 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (105 mg). $^1$H NMR (400 MHz, CDCl$_3$): 7.19 (d, J=8.4Hz, 2H), 6.84 (d, J=8.5 Hz, 2H), 4.30–4.26 (m, 1H), 3.40 (s, 2H), 2.75–2.70 (m, 2H), 2.40–2.20 (m, 7H), 2.06–1.93 (m, 2H), 1.86–1.68 (m, 5H), 1.59–1.37 (m, 6H), 0.92–0.86 (m, 3H).

Example 29

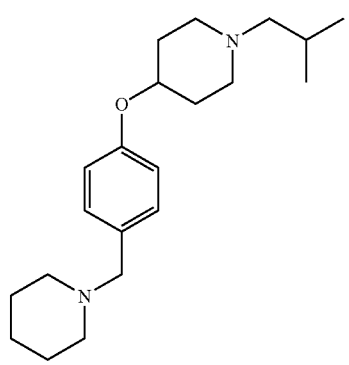

K$_i$ = 0.9 nM

1-[4-(1-Isobutyl-piperidin-4-yloxy)-benzyl]-piperidine

Phenylsilane (0.068 mL) was added dropwise to a solution of the product of Example 9 (137 mg), isobutyraldehyde (0.091 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (91 mg). $^1$H NMR (400 MHz, CDCl$_3$): 7.19 (d, J=8.6 Hz, 2H), 6.84 (d, J=8.6 Hz, 2H), 4.28–4.23 (m, 1H), 3.39 (s, 2H), 2.72–2.69 (m, 2H), 2.35 (bs, 4H), 2.21–2.16 (m, 2H), 2.09 (d, 2H), 2.01–1.95 (m, 3H), 1.59–1.53 (m, 3H), 1.44–1.38 (m, 2H), 0.90 (d, J=6.6 Hz, 6H).

Example 30

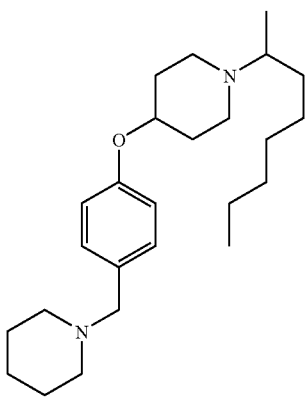

$K_i = 16$ nM

1-{4-[1-(1-Methyl-heptyl)-piperidin-4-yloxy]-benzyl}-piperidine

Phenylsilane (0.068 mL) was added dropwise to a solution of the product of Example 9 (137 mg), 2-octanone (0.156 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (228 mg). $^1$H NMR (400 MHz, CDCl$_3$): 7.19 (d, J=8.5 Hz, 2H), 6.84 (d, J=8.6 Hz, 2H), 4.28–4.22 (m, 1H), 3.40 (s, 2H), 2.79–2.72 (m, 2H), 2.59–2.55 (m, 1H), 2.46–2.31 (m, 6H), 1.83–1.73 (m, 2H), 1.57–1.53 (m, 4H), 1.43–1.38 (m, 8H), 1.32–1.21 (m, 10H), 0.98 (d, J=6.5 Hz, 3H), 0.89 (t, J=6.8 Hz, 3H).

Example 31

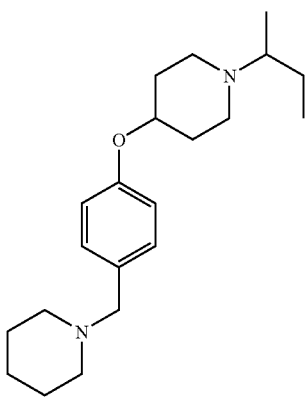

$K_i = 0.5$ nM

4-[4-(1-sec-Butyl-piperidin-4-yloxy)-benzyl]-morpholine

Phenylsilane (0.068 mL) was added dropwise to a solution of the product of Example 9 (137 mg), 2-butanone (0.089 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (164 mg). $^1$H NMR (400 MHz, CDCl$_3$): 7.19 (d, J=8.6 Hz, 2H), 6.84 (d, J=8.6 Hz, 2H), 4.28–4.22 (m, 1H), 3.39 (s, 2H), 2.89–2.72 (m, 2H), 2.50–2.31 (m, 6H), 1.98–1.95 (m, 2H), 1.83–1.72 (m, 2H), 1.59–1.53 (m, 6H), 1.43–1.37 (m, 2H), 1.34–1.23 (m, 1H), 0.98 (d, J=6.5 Hz, 3H), 0.90 (t, J=7.4 Hz, 3H).

Example 32

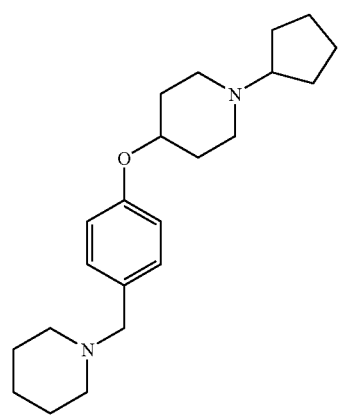

$K_i = 0.7$ nM

1-[4-(1-Cyclopentyl-piperidin-4-yloxy)-benzyl]-piperidine

Phenylsilane (0.068 mL) was added dropwise to a solution of the product of Example 9 (137 mg), cyclopentanone (0.088 mL) and scandium trifluoromethanesulfonate (13 mg) in THF (1 mL). After 16 h, the resulting mixture was filtered through a pad of celite, and the pad was washed with DCM (3×3 mL). The combined filtrates were chromatographed (0.5–5.5% 2 M methanolic ammonia/DCM), giving the title compound as a colorless oil (250 mg). $^1$H NMR (400 MHz, CDCl$_3$): 7.19 (d, J=8.5 Hz, 2H), 6.84 (d, J=8.6 Hz, 2H), 4.34–4.23 (m, 1H), 3.39 (s, 2H), 2.87–2.73 (m, 2H), 2.55–2.47 (m, 1H), 2.40–2.26 (m, 6H), 2.05–1.95 (m, 2H), 1.91–1.79 (m, 4H), 1.73–1.49 (m, 8H), 1.46–1.37 (m, 4H).

Example 33

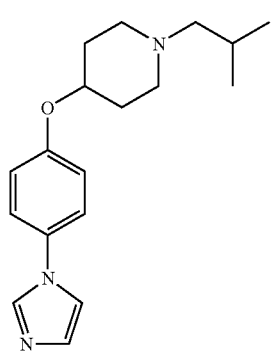

$K_i = 9$ nM 4-(4-Imidazol-1-yl-phenoxy)-1-isobutyl-piperidine

A solution of the product of Example 6 (130 mg), cyclohexanone (0.06 mL), and dibutyltin dichloride (3 mg) in THF (0.1 mL) was treated with phenylsilane (0.07 mL). After 16 h, the resulting mixture was chromatographed (0–8% 2M methanolic ammonia/DCM), giving the title compound as a waxy solid (18 mg). $^1$H NMR (400 MHz, CDCl$_3$): 7.75 (t, J=1.2 Hz, 1H), 7.28 (d, J=9.0 Hz, 2H), 7.20 (t, J=1.4 Hz, 1H), 7.18 (t, J=1.2 Hz, 1H), 6.99 (d, J=8.8 Hz, 2H), 4.35–4.27 (m, 1H), 2.76–2.67 (m, 2H), 2.26–2.18 (m, 2H), 2.10 (d, J=7.24 Hz, 2H), 2.05–1.96 (m, 2H), 1.87–1.73 (m, 3H), 0.90 (d, J=6.5 Hz, 6H).

Example 34

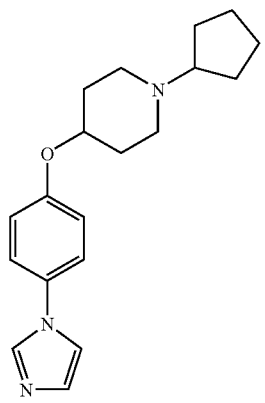

K$_i$ = 1.4 nM

1-Cyclopentyl-4-(4-imidazol-1-yl-phenoxy)-piperidine

A solution of the product of Example 6 (130 mg), isobutyraldehyde (0.06 mL), and dibutyltin dichloride (3 mg) in THF (0.1 mL) was treated with phenylsilane (0.07 mL). After 16 h, the resulting mixture was chromatographed (0–8% 2M methanolic ammonia/DCM), giving the title compound as a waxy solid (57 mg). $^1$H NMR (400 MHz, CDCl$_3$): 7.75 (t, J=1.2 Hz, 1H), 7.28 (d, J=9.0 Hz, 2H), 7.20 (t, J=1.2 Hz, 1H), 7.17 (t, J=1.2 Hz, 1H), 6.99 (d, J=9.0 Hz, 2H), 4.39–4.29 (m, 1H), 2.87–2.77 (br m, 1H), 2.57–2.48 (m, 1H), 2.40–2.30 (m, 2H), 2.08–1.99 (m, 2H), 1.94–1.82 (m, 5H), 1.75–1.64 (m, 2H), 1.61–1.61 (m, 2H), 1.47–1.37 (m, 2H).

Example 35

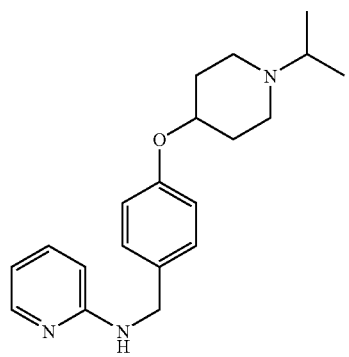

K$_i$ = 3.4 nM

[4-(1-Isopropyl-piperidin-4-yloxy)-benzyl]-pyridin-2-yl-amine

A solution of the product of Example 2 (522 mg), 2-aminopyridine (230 mg), and acetic acid (0.01 3 mL) in DCM (7 mL) was treated with sodium triacetoxyborohydride (720 mg). After 16 h, the resulting mixture was treated with 10% sodium hydroxide (8 mL), and the mixture was extracted with DCM (3×10 mL). The combined organic phases were dried (sodium sulfate) and evaporated. Chromatography of the residue (1–7% 2M methanolic ammonia/DCM) gave the title compound as a yellow solid (417 mg). $^1$H NMR (400 MHz, CDCl$_3$): 8.10 (m, 1H), 7.40 (m, 1H), 7.28–7.24 (m, 2H), 6.9–6.85 (m, 2H), 6.58 (m, 1H), 6.37 (m, 1H), 4.77 (m 1H), 4.41 (d, J=5.8 Hz, 2H), 4.28 (m, 1H), 2.82–2.71 (m, 4H), 2.39 (m, 3H), 2.05–1.97 (m, 3H), 1.85–1.76 (m, 3H), 1.06 (d, J=6.6 Hz, 6H).

Example 36

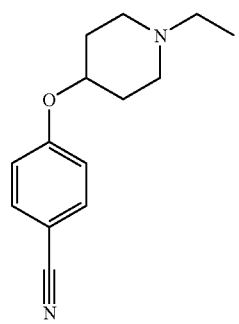

K$_i$ = 600 nM 4-(1-Ethyl-piperidin-4-yloxy)-benzonitrile

A solution of the product of Example 5 (226 mg), acetaldehyde (0.5 mL), and acetic acid (0.09 mL) in DCM (3 mL) was treated with sodium triacetoxyborohydride (360 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (67 mg). $^1$H NMR (400 MHz, CDCl$_3$): 7.53 (d, J=8.8 Hz, 2H), 6.91 (d, J=8.8 Hz, 2H), 4.37 (m, 1H), 2.71 (m, 2H), 2.41 (q, J=7.1, 2H), 2.28 (m, 2H), 1.99 (m, 2H), 1.82 (m, 2H), 1.07 (t, J=7.1, 3H).

Example 37

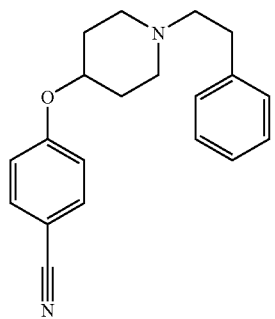

K$_i$ = 6000 nM 4-(1-Phenethyl-piperidin-4-yloxy)-benzonitrile

A solution of the product of Example 5 (203 mg), phenylacetaldehyde (0.14 mL), and acetic acid (0.08 mL) in DCM (3 mL) was treated with sodium triacetoxyborohydride (320 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (145 mg). $^1$H NMR (400 MHz, CDCl$_3$): 7.58 (d, J=8.8 Hz, 2H), 7.32–7.28 (m, 2H), 7.21 (m, 3H), 6.94 (d, J=8.8 Hz, 2H), 4.45 (br,1H), 2.84 (br, 4H), 2.66 (br, 2H), 2.42 (br, 1.5H), 2.04 (br, 1.5H), 1.91 (br, 2H), 1.55 (br, 1H).

Example 38

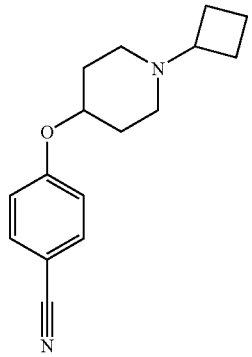

$K_i = 24$ nM 4-(1-Cyclobutyl-piperidin-4-yloxy)-benzonitrile

A solution of the product of Example 5 (206 mg), cyclobutanone (0.1 mL), and acetic acid (0.08 mL) in DCM (3 mL) was treated with sodium triacetoxyborohydride (320 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (66 mg). $^1$H NMR (400 MHz, CDCl$_3$): 7.58 (d, J=8.8 Hz, 2H), 6.93 (d, J=8.8 Hz, 2H), 4.41 (br, 1H), 2.81–2.54 (br, m, 3H), 2.23–1.46 (br, m, 12H).

Example 39

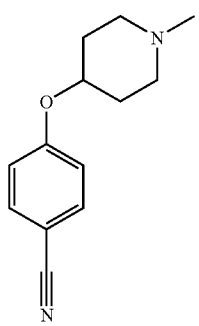

$K_i = 5000$ nM 4-(1-Methyl-piperidin-4-yloxy)-benzonitrile

A solution of the product of Example 5 (213 mg), paraformaldehyde (0.52 g), and acetic acid (0.08 mL) in DCM (3 mL) was treated with sodium triacetoxyborohydride (340 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (91 mg). $^1$H NMR (400 MHz, CDCl$_3$): 7.57 (d, J=9.1 Hz, 2H), 6.93 (d, J=9.1 Hz, 2H), 4.40 (m, 1H), 2.69 (br, 2H), 2.37–2.29 (br, 2H), 2.32 (s, 3H), 2.03 (m, 2H), 1.87 (m, 2H).

Example 40

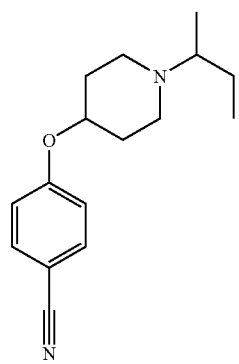

$K_i = 26$ nM 4-(1-sec-Butyl-piperidin-4-yloxy)-benzonitrile

A solution of the product of Example 5 (211 mg), 2-butanone (0.13 mL), and acetic acid (0.07 mL) in DCM (3 mL) was treated with sodium triacetoxyborohydride (330 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (91 mg). $^1$H NMR (400 MHz, CDCl$_3$): 7.56 (d, J=9.1 Hz, 2H), 6.93 (d, J=9.1 Hz, 2H), 4.36 (br, 1H), 2.77 (br, 2H), 2.50 (br, 2H), 2.37 (br, 1H), 2.02 (br, 2H), 1.81 (br, 2H), 1.58 (br, 1H), 1.30 (m, 1H), 1.0 (br, d, J=6.1 Hz, 3H), 0.91 (t, J=7.3 Hz, 3H).

Example 41

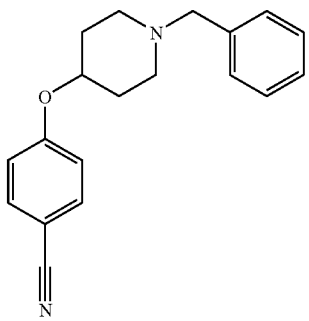

$K_i = 5000$ nM 4-(1-Benzyl-piperidin-4-yloxy)-benzonitrile

A solution of the product of Example 5 (203 mg), benzaldehyde (0.13 mL), and acetic acid (0.07 mL) in DCM (3 mL) was treated with sodium triacetoxyborohydride (330 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (112 mg). $^1$H NMR (400 MHz, CDCl$_3$): 7.56 (d, J=8.8 Hz, 2H), 7.33 (m, 3H), 7.27 (m, 2H), 6.93 (d, J=8.8 Hz, 2H), 4.40 (br, 1H), 3.54 (br, 2H), 2.73 (br, 2H), 2.32 (br, 2H), 1.99 (br, 2H), 1.84 (br, 2H), 1.56 (br, 1H).

Example 42

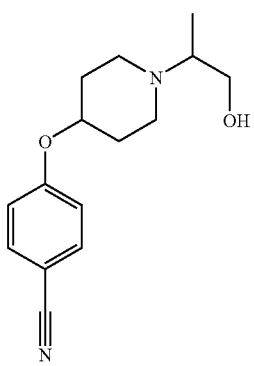

K$_i$ = 2000 nM

4-[1-(2-Hydroxy-1-methyl-ethyl)-piperidin-4-yloxy]-benzonitrile

A solution of the product of Example 5 (205 mg), 1-hydroxy-2-propanone (0.14 mL), and acetic acid (0.08 mL) in DCM (3 mL) was treated with sodium triacetoxyborohydride (330 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (161 mg). $^1$H NMR (400 MHz, CDCl$_3$): 7.57 (d, J=8.8 Hz, 2H), 6.93 (d, J=8.8 Hz, 2H), 4.42 (m, 1H), 3.42 (m, 1H), 3.32 (m, 1H), 2.88 (m, 2H), 2.64 (m, 2H), 2.33 (m, 1H), 2.03 (m, 2H), 1.84 (m, 2H), 0.92 (d, J=6.6 Hz, 3H).

Example 43

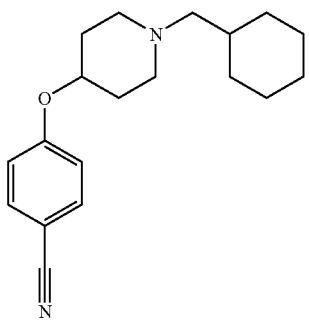

K$_i$ = 6000 nM 4-(1-Cyclohexylmethyl-piperidin-4-yloxy)-benzonitrile

A solution of the product of Example 5 (221 mg), cyclohexanecarboxaldehyde (0.2 mL), and acetic acid (0.08 mL) in DCM (3 mL) was treated with sodium triacetoxyborohydride (340 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (205 mg). $^1$H NMR (400 MHz, CDCl$_3$): 7.57 (d, J=9.1 Hz, 2H), 6.93 (d, J=9.1 Hz, 2H), 4.37 (br, 1H), 2.69 (br, 2H), 2.22 (br, 2H), 2.14 (br, 2H), 1.98 (br, 2H), 1.86–1.63 (m, 7H), 1.47 (br, 1H), 1.29–1.10 (m, 3H), 0.88 (m, 2H).

Example 44

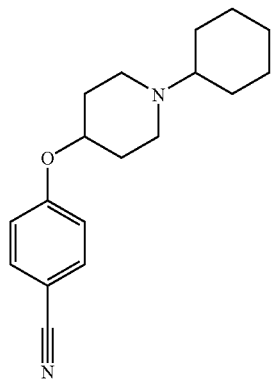

K$_i$ = 52 nM 4-(1-Cyclohexyl-piperidin-4-yloxy)-benzonitrile

A solution of the product of Example 5 (202 mg), cyclohexanone (0.17 mL), and acetic acid (0.08 mL) in DCM (3 mL) was treated with sodium triacetoxyborohydride (340 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (241 mg). $^1$H NMR (400 MHz, CDCl$_3$): 7.56 (d, J=8.8 Hz, 2H), 6.93 (d, J=8.8 Hz, 2H), 4.37 (m, 1H), 2.84 (m, 2H), 2.47 (m, 2H), 2.32 (br, 1H), 2.01 (br, 2H), 1.89–1.77 (m, 6H), 1.63 (m, 1H), 1.30–1.17 (m, 4H), 1.10 (m, 1H).

Example 45

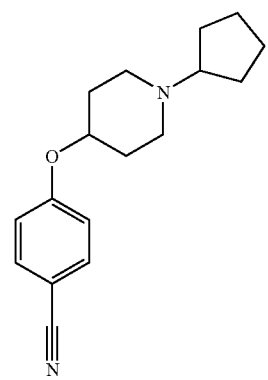

K$_i$ = 19 nM 4-(1-Cyclopentyl-piperidin-4-yloxy)-benzonitrile

A solution of the product of Example 5 (210 mg), cyclopentanone (0.14 mL), and acetic acid (0.08 mL) in DCM (3 mL) was treated with sodium triacetoxyborohydride (330 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (237 mg). $^1$H NMR (400 MHz, CDCl$_3$): 7.57 (d, J=8.8 Hz, 2H), 6.94 (d, J=8.9 Hz, 2H), 4.40 (br, 1H), 2.91–2.23 (brr, m, 5H), 2.13–1.35 (m, 12H).

Example 46

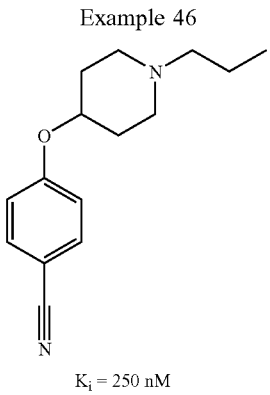

K$_i$ = 250 nM 4-(1-Propyl-piperidin-4-yloxy)-benzonitrile

A solution of the product of Example 5 (211 mg), propanaldehyde (0.15 mL), and acetic acid (0.07 mL) in DCM (3 mL) was treated with sodium triacetoxyborohydride (330 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (64 mg). $^1$H NMR (400 MHz, CDCl$_3$): 7.57 (d, J=9.1 Hz, 2H), 6.93 (d, J=9.1 Hz, 2H), 4.42 (br, 1H), 2.76 (br, 2H), 2.35 (br, 3H), 2.05 (br, 2H), 1.87 (br, 2H), 1.56 (br, 2H), 0.92 (t, J=7.3 Hz, 3H).

Example 47

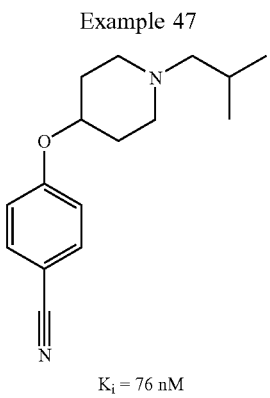

K$_i$ = 76 nM 4-(1-Isobutyl-piperidin-4-yloxy)-benzonitrile

A solution of the product of Examples 5 (202 mg), isobutyraldehyde (0.21 mL), and acetic acid (0.07 mL) in DCM (3 mL) was treated with sodium triacetoxyborohydride (360 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (211 mg). $^1$H NMR (400 MHz, CDCl$_3$): 7.56 (d, J=9.1 Hz, 2H), 6.93 (d, J=9.1 Hz, 2H), 4.37 (br, 1H), 2.69 (br, 2H), 2.22 (br, 2H), 2.09 (br, 2H), 1.98 (br, 2H), 187–1.73 (m, 3H), 0.90 (d, br, J=7.3 Hz, 6H).

Example 48

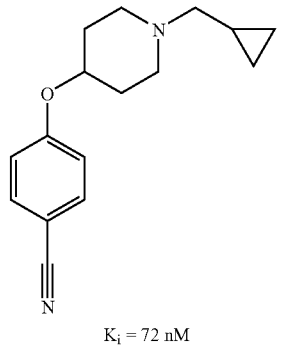

K$_i$ = 72 nM 4-(1-Cyclopropylmethyl-piperidin-4-yloxy)-benzonitrile

A solution of the product of Example 5 (215 mg), cyclopropanecarboxaldehyde (0.16 mL), and acetic acid (0.07 mL) in DCM (3 mL) was treated with sodium triacetoxyborohydride (340 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a white solid (173 mg). $^1$H NMR (400 MHz, CDCl$_3$): 7.56 (d, J=9.1 Hz, 2H), 6.93 (d, J=9.1 Hz, 2H), 4.40 (m, 1H), 2.83 (m, 2H), 2.40 (m, 2H), 2.29 (d, J=6.6 Hz, 2H), 2.03 (m, 2H), 1.87 (m, 2H), 0.88 (m, 1H), 0.52 (m, 2H), 0.11 (m, 2H).

Example 49

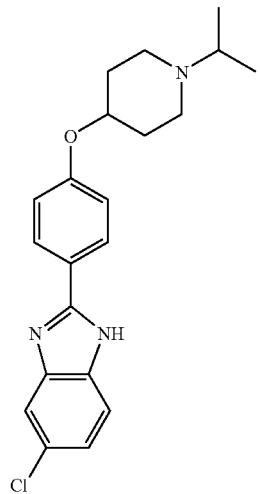

K$_i$ = 14 nM

5-Chloro-2-[4-(1-isopropyl-piperidin-4-yloxy)-phenyl]-1H-benzoimidazole

A solution of the product of Example 2 (260 mg), 4-chloro-benzene-1,2-diamine (156 mg), and sodium metabisulfite (280 mg) in DMA (2 mL) was heated to 100° C. for 12 h. The resulting mixture was chromatographed (1–7% 2M methanolic ammonia/DCM), giving the title compound as a pink solid (191 mg). $^1$H NMR (400 MHz, CDCl$_3$): 7.99 (d, J=9.1 Hz, 2H), 7.54 (m, 1H), 7.51 (m, 1H), 7.21 (m, 1H), 7.09 (d, J=9.1 Hz, 2H), 4.51 (m, 1H), 2.84 (m, 2H), 2.77 (m, 1H), 2.51 (m, 2H), 2.07 (m, 2H), 1.82 (m, 2H), 1.10 (d, J=6.6 Hz, 6H).

Example 50

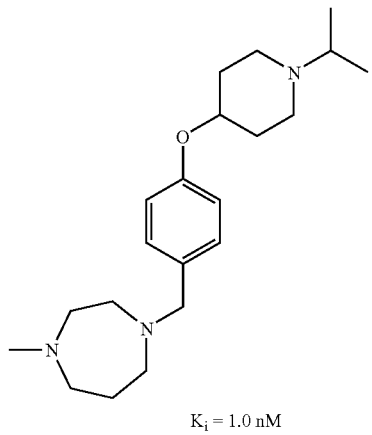

$K_i$ = 1.0 nM

1-[4-(1-Isopropyl-piperidin-4-yloxy)-benzyl]-4-methyl-[1,4]diazepane

A solution of the product of Example 2 (171 mg), N-methyl homopiperazine (0.09 mL), and acetic acid (0.07 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (121 mg). $^1$H NMR (400 MHz, CDCl$_3$): 7.22 (d, J=8.6 Hz, 2H), 6.84 (d, J=8.6 Hz, 2H), 4.26 (m, 1H), 3.55 (s, 2H), 2.82–2.72 (m, 3H), 2.71–2.63 (m, 6H), 2.61–2.57 (m, 2H), 2.41–2.36 (m, 2H), 2.35 (s, 3H), 2.00 (m, 2H), 1.85–1.76 (m, 4H), 1.06 (d, J=6.6 Hz, 6H).

Example 51

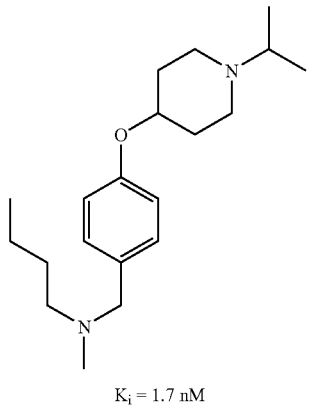

$K_i$ = 1.7 nM

Butyl-[4-(1-isopropyl-piperidin-4-yloxy)-benzyl]-methyl-amine

A solution of the product of Example 2 (167 mg), butyl-methyl-amine (0.08 mL), and acetic acid (0.07 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (157 mg). $^1$H NMR (400 MHz, CDCl$_3$): 7.19 (d, J=8.6 Hz, 2H), 6.85 (d, J=8.6 Hz, 2H), 4.27 (m, 1H), 3.40 (s, 2H), 2.82–2.71 (m, 3H), 2.39 (m, 2H), 2.34 (m, 2H), 2.16 (s, 3H), 2.00 (m, 2H), 1.85–1.76 (m, 2H), 1.52–1.45 (m, 2H), 1.38–1.27 (m, 2H) 1.06 (d, J=6.6 Hz, 6H), 0.90 (t, J=7.3 Hz, 3H).

Example 52

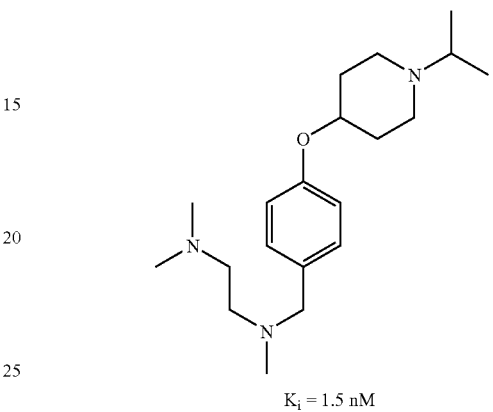

$K_i$ = 1.5 nM

N-[4-(1-Isopropyl-piperidin-4-yloxy)-benzyl]-N,N', N'-trimethyl-ethane-1,2-diamine A solution of the product of Example 2 (171 mg), N,N, N'-trimethyl-ethane-1,2-diamine (0.09 mL), and acetic acid (0.07 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (126 mg). $^1$H NMR (400 MHz, CDCl$_3$): 7.19 (d, J=8.6 Hz, 2H), 6.84 (d, J=8.6 Hz, 2H), 4.26 (m, 1H), 3.44 (s, 2H), 2.82–2.71 (m, 3H), 2.48–2.34 (m, 6H), 2.22 (s, 3H), 2.20 (s, 6H), 2.04–1.96 (m, 2H), 1.85–1.75 (m, 2H), 1.06 (d, J=6.6 Hz, 6H).

Example 53

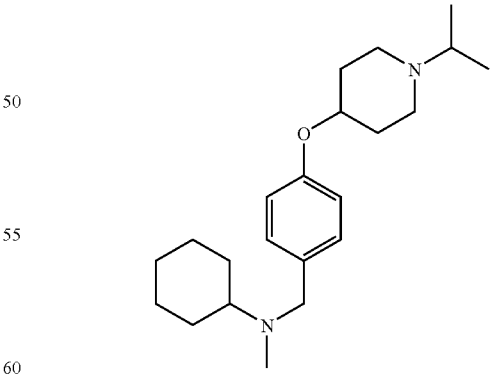

$K_i$ = 1.7 nM

Cyclohexyl-[4-(1-isopropyl-piperidin-4-yloxy)-benzyl]-methyl-amine

A solution of the product of Example 2 (169 mg), cyclohexyl-methyl-amine (0.09 mL), and acetic acid (0.07 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (165 mg). $^1$H NMR (400 MHz, CDCl$_3$): 7.19 (d, J=8.6 Hz, 2H), 6.84 (d, J=8.6 Hz, 2H), 4.26 (m, 1H), 3.48 (s, 2H), 2.82–2.70 (m, 3H), 2.46–2.33 (m, 3H), 2.17 (s, 3H), 2.04–1.96 (m, 2H), 1.89–1.76 (m, 6H), 1.62 (m, 1H), 1.34–1.15 (m, 4H) 1.05 (d, J=6.6 Hz, 6H).

Example 54

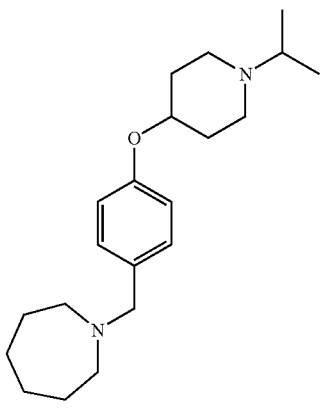

$K_i$ = 1.2 nM

1-[4-(1-Isopropyl-piperidin-4-yloxy)-benzyl]-azepane

A solution of the product of Example 2 (167 mg), hexamethyleneimine (0.08 mL), and acetic acid (0.07 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (163 mg). $^1$H NMR (400 MHz, CDCl$_3$): 7.22 (d, J=8.6 Hz, 2H), 6.84 (d, J=8.6 Hz, 2H), 4.26 (m, 1H), 3.56 (s, 2H), 2.85–2.71 (m, 3H), 2.60 (m, 4H), 2.38 (m, 2H), 2.04–1.96 (m, 2H), 1.85–1.76 (m, 2H), 1.60 (m, 9H), 1.06 (d, J=6.6 Hz, 6H).

Example 55

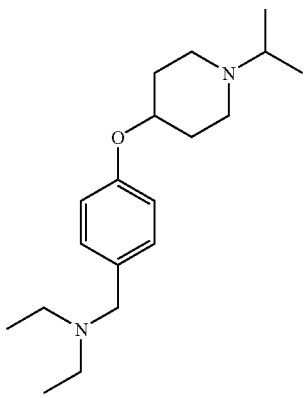

$K_i$ = 1.9 nM

Diethyl-[4-(1-isopropyl-piperidin-4-yloxy)-benzyl]-amine

A solution of the product of Example 2 (170 mg), diethylamine (0.08 mL), and acetic acid (0.07 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (78 mg). $^1$H NMR (400 MHz, CDCl$_3$): 7.21 (d, J=8.6 Hz, 2H), 6.84 (d, J=8.6 Hz, 2H), 4.26 (m, 1H), 3.49 (s, 2H), 2.82–2.70 (m, 4H), 2.50 (q, J=7.1 Hz, 4H), 2.37 (m, 2H), 2.04–1.96 (m, 2H), 1.85–1.76 (m, 2H), 1.60 (m, 9H), 1.07–1.00 (m, 12H).

Example 56

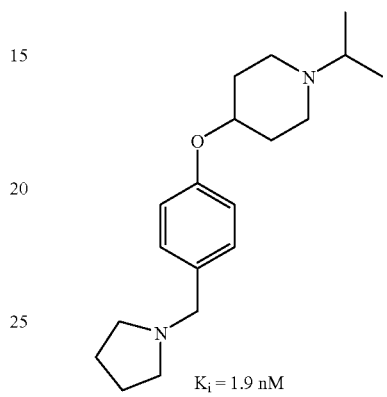

$K_i$ = 1.9 nM

1-Isopropyl-4-(4-pyrrolidin-1-ylmethyl-phenoxy)-piperidine

A solution of the product of Example 2 (169 mg), pyrrolidine (0.06 mL), and acetic acid (0.07 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (144 mg). $^1$H NMR (400 MHz, CDCl$_3$): 7.21 (d, J=8.8 Hz, 2H), 6.84 (d, J=8.8 Hz, 2H), 4.26 (m, 1H), 3.53 (s, 2H), 2.82–2.71 (m, 3H), 2.48 (m, 4H), 2.37 (m, 2H), 2.03–1.96 (m, 2H), 1.85–1.74 (m, 6H), 1.05 (d, J=6.6 Hz, 6H).

Example 57

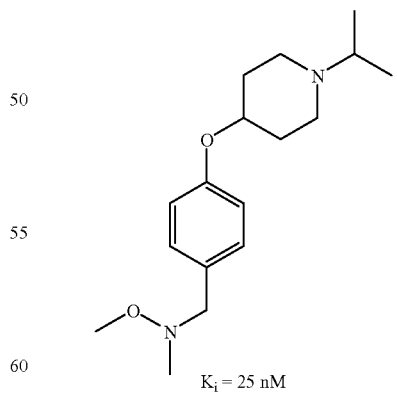

$K_i$ = 25 nM

N-[4-(1-Isopropyl-piperidin-4-yloxy)-benzyl]-O,N-dimethyl-hydroxylamine

A solution of the product of Example 2 (170 mg) and O,N-dimethyl-hydroxylamine hydrochloride (0.15 g) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (179 mg). $^1$H NMR (400 MHz, CDCl$_3$): 7.24 (d, J=8.8 Hz, 2H), 6.85 (d, J=8.8 Hz, 2H), 4.27 (m, 1H), 3.70 (s, 2H), 3.37 (s, 3H), 2.81–2.70 (m, 3H), 2.58 (s, 3H), 2.48 (m, 4H), 2.37 (m, 2H), 2.03–1.96 (m, 2H), 1.85–1.76 (m, 2H), 1.05 (d, J=6.6 Hz, 6H).

Example 58

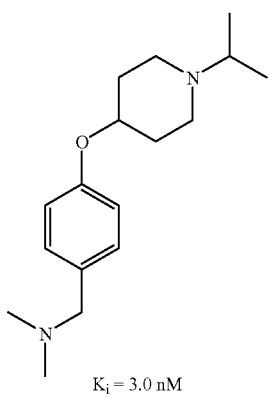

K$_i$ = 3.0 nM

[4-(1-Isopropyl-piperidin-4-yloxy)-benzyl]-dimethyl-amine

A solution of the product of Example 2 (170 mg) and dimethylamine hydrochloride (0.12 g) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (163 mg). $^1$H NMR (400 MHz, CDCl$_3$): 7.18 (d, J=8.6 Hz, 2H), 6.85 (d, J=8.6 Hz, 2H), 4.27 (m, 1H), 3.34 (s, 2H), 3.37 (s, 3H), 2.81–2.70 (m, 3H), 2.38 (m, 2H), 2.21 (s, 6H), 2.05–1.96 (m, 2H), 1.85–1.75 (m, 2H), 1.05 (d, J=6.6 Hz, 6H).

Example 59

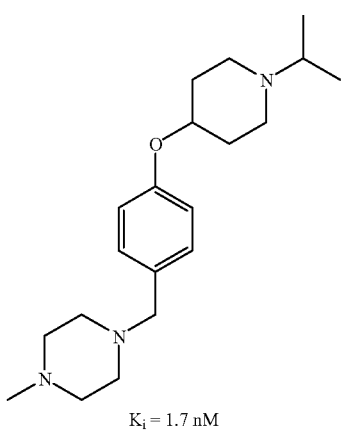

K$_i$ = 1.7 nM

1-[4-(1-Isopropyl-piperidin-4-yloxy)-benzyl]-4-methyl-piperazine

A solution of the product of Example 2 (173 mg), N-methylpiperazine (0.08 mL), and acetic acid (0.08 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (217 mg). $^1$H NMR (400 MHz, CDCl$_3$): 7.19 (d, J=8.6 Hz, 2H), 6.83 (d, J=8.6 Hz, 2H), 4.26 (m, 1H), 3.42 (s, 2H), 2.81–2.70 (m, 3H), 2.55–2.33 (m, 8H), 2.26 (s, 3H), 2.03–1.97 (m, 2H), 1.84–1.74 (m, 2H), 1.04 (d, J=6.6 Hz, 6H).

Example 60

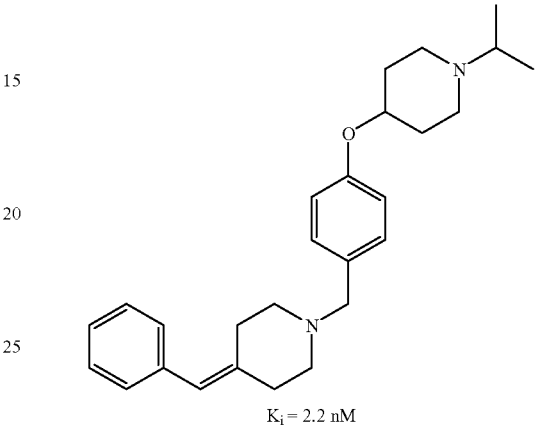

K$_i$ = 2.2 nM

4-[4-(4-Benzylidene-piperidin-1-ylmethyl)-phenoxy]-1-isopropyl-piperidine

A solution of the product of Example 2 (136 mg), 4-benzylidene-piperidine (94 mg), and acetic acid (0.05 mL) in DCM (3 mL) was treated with sodium triacetoxyborohydride (190 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (54 mg). $^1$H NMR (400 MHz, CDCl$_3$): 7.32–7.27 (m, 2H), 7.23–7.16 (m, 5H), 6.86 (d, J=8.6 Hz, 2H), 6.27 (s, 1H), 4.28 (m, 1H), 3.46 (s, 2H), 2.83–2.71 (m, 3H), 2.54–2.49 (m, 4H), 2.43–2.35 (m, 6H), 2.05–1.97 (m, 2H), 1.86–1.76 (m, 2H), 1.06 (d, J=6.6 Hz, 6H).

Example 61

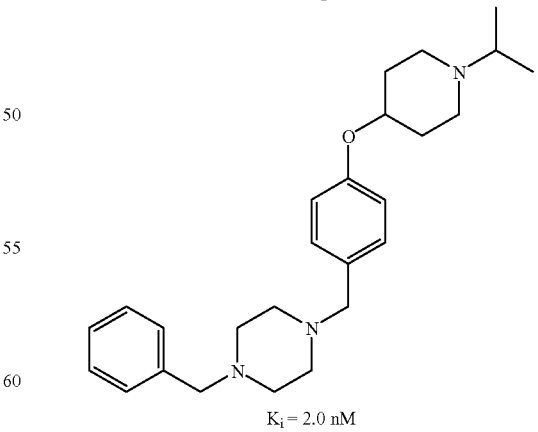

K$_i$ = 2.0 nM

1-Benzyl-4-[4-(1-isopropyl-piperidin-4-yloxy)-benzyl]-piperazine

A solution of the product of Example 2 (188 mg), N-benzylpiperazine (0.13 mL), and acetic acid (0.06 mL) in DCM (3 mL) was treated with sodium triacetoxyborohydride (260 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (239 mg). $^1$H NMR (400 MHz, CDCl$_3$): 7.31–7.29 (m, 4H), 7.25–7.23 (m, 1H), 7.18 (d, J=8.6 Hz, 2H) 6.84 (d, J=8.6 Hz, 2H), 4.26 (m, 1H), 3.50 (s, 2H), 3.43 (s, 2H), 2.82–2.70 (m, 3H), 2.54–2.34 (m, 9H), 2.03–1.96 (m, 2H), 1.84–1.75 (m, 2H), 1.06 (d, J=6.6 Hz, 6H).

Example 62

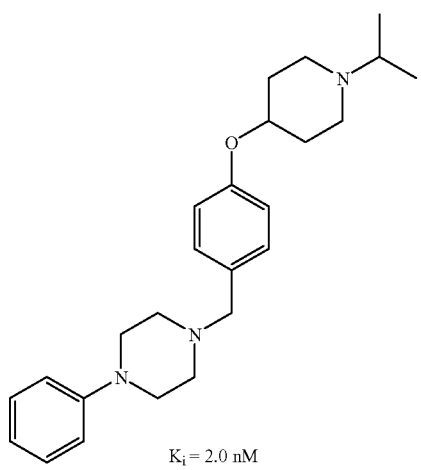

$K_i = 2.0$ nM

1-[4-(1-Isopropyl-piperidin-4-yloxy)-benzyl]-4-phenyl-piperazine

A solution of the product of Example 2 (140 mg), N-phenylpiperazine (0.09 mL), and acetic acid (0.05 mL) in DCM (3 mL) was treated with sodium triacetoxyborohydride (190 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (78 mg). $^1$H NMR (400 MHz, CDCl$_3$): 7.30–7.22 (m, 4H), 6.65–6.82 (m, 5H), 4.29 (m, 1H), 3.50 (s, 2H), 3.19 (m, 2H), 3.16–3.12 (m, 2H), 2.83–2.71 (m, 3H), 2.59 (m, 2H), 2.39 (m, 2H), 2.06–1.99 (m, 2H), 1.87–1.78 (m, 2H), 1.07 (d, J=6.6 Hz, 6H).

Example 63

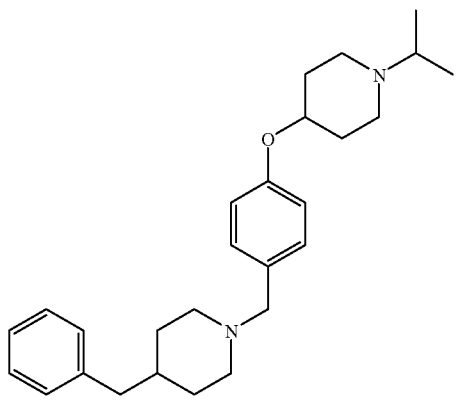

$K_i = 1.5$ nM

1-[4-(1-isopropyl-piperidin-4-yloxy)-benzyl]-4-benzyl-piperidine

A solution of the product of Example 2 (188 mg), N-benzylpiperidine (0.13 mL), and acetic acid (0.05 mL) in DCM (3 mL) was treated with sodium triacetoxyborohydride (250 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (160 mg). $^1$H NMR (400 MHz, CDCl$_3$): 7.29–7.23 (m, 3H), 7.19–7.10 (m, 4H), 6.83 (m, 2H), 4.26 (m, 1H), 3.39 (s, 2H), 2.87–2.70 (m, 5H), 2.52 (d, J=7.1 Hz, 2H), 2.38 (m, 2H), 2.03–1.96 (m, 2H), 1.59 (m, 2H), 1.50 (m, 1H), 1.29 (m, 2H), 1.06 (d, J=6.6 Hz, 6H).

Example 64

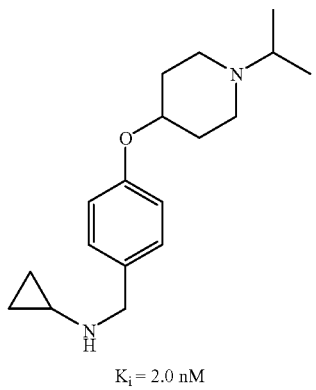

$K_i = 2.0$ nM

Cyclopropyl-[4-(1-isopropyl-piperidin-4-yloxy)-benzyl]-amine

A solution of the product of Example 2 (250 mg), cyclopropylamine (0.10 mL), and acetic acid (0.07 mL) in DCM (3 mL) was treated with sodium triacetoxyborohydride (340 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (88 mg). $^1$H NMR (400 MHz, CDCl$_3$): 7.19 (d, J=8.6 Hz, 2H), 6.84 (d, J=8.6 Hz, 2H), 4.25 (m, 1H), 3.74 (s, 2H), 2.81–2.69 (m, 3H), 2.37 (m, 2H), 2.12 (m, 1H), 2.03–1.95 (m, 2H), 1.83–1.74 (m, 2H), 1.04 (d, J=6.6 Hz, 6H), 0.44–0.33 (m, 4H).

Example 65

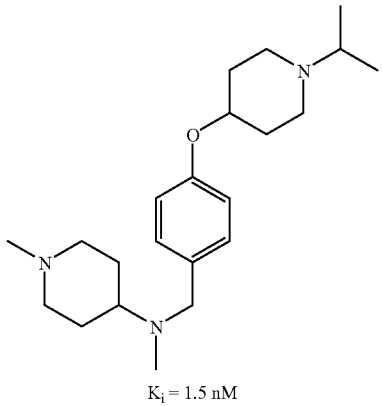

$K_i = 1.5$ nM

[4-(1-Isopropyl-piperidin-4-yloxy)-benzyl]-methyl-(1-methyl-piperidin-4-yl)-amine A solution of the product of Example 2 (146 mg), 1-methyl-4-(methylamino)piperidine (0.09 mL), and acetic acid (0.09 mL) in DCM (3 mL) was treated with sodium triacetoxyborohydride (200 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (137 mg). $^1$H NMR (400 MHz, CDCl$_3$): 7.16 (d, J=8.6 Hz, 2H), 6.82 (d, J=8.6 Hz, 2H), 4.24 (m, 1H), 3.47 (s, 2H), 2.88 (m, 2H), 2.79–2.68 (m, 3H), 2.43–2.32 (m, 3H), 2.23 (s, 3H), 2.15 (s, 3H), 2.01–1.94 (m, 2H), 1.89 (m, 2H), 1.82–1.73 (m, 4H), 1.69–1.59 (m, 2H) 1.03 (d, J=6.6 Hz, 6H).

Example 66

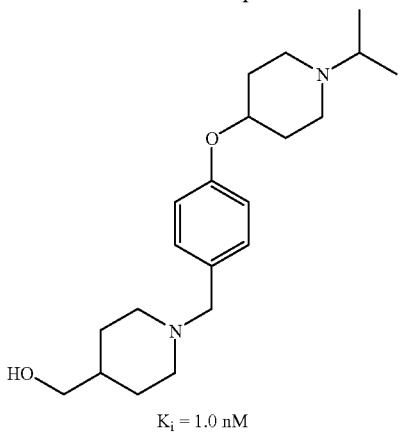

$K_i = 1.0$ nM

{1-[4-(1-Isopropyl-piperidin-4-yloxy)-benzyl]-piperidin-4-yl}-methanol

A solution of the product of Example 2 (158 mg), 4-piperidinemethanol (78 mg), and acetic acid (0.08 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (166 mg). $^1$H NMR (400 MHz, CDCl$_3$): 7.17 (d, J=8.6 Hz, 2H), 6.82 (d, J=8.6 Hz, 2H), 4.25 (m, 1H), 3.24 (d, J=6.6 Hz, 2H), 3.39 (s, 2H), 2.87 (m, 2H), 2.80–2.69 (m, 3H), 2.37 (m, 2H), 2.02–1.94 (m, 2H), 1.90 (m, 2H), 1.83–1.74 (m, 2H), 1.69 (m, 2H) 1.45 (m, 1H), 1.23 (m, 2H), 1.04 (d, J=6.6 Hz, 6H).

Example 67

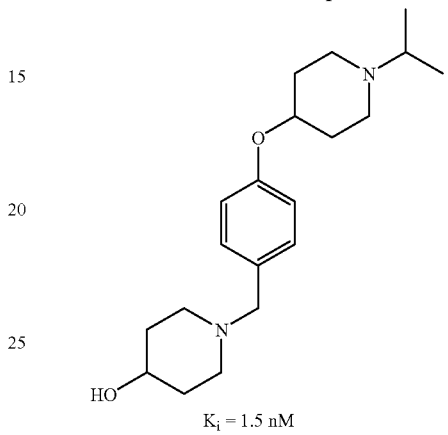

$K_i = 1.5$ nM

1-[4-(1-Isopropyl-piperidin-4-yloxy)-benzyl]-piperidin-4-ol

A solution of the product of Example 2 (167 mg), 4-hydroxypiperidine (73 mg), and acetic acid (0.08 mL) in DCM (3 mL) was treated with sodium triacetoxyborohydride (220 mg). After 16 h, the resulting mixture was treated with 10% sodium hydroxide (5 mL), and the mixture was extracted with DCM (3×10 mL). The combined organic phases were dried (sodium sulfate) and evaporated. Chromatography of the residue (1–7% 2M methanolic ammonia/DCM) gave the title compound as a clear oil (168 mg). $^1$H NMR (400 MHz, CDCl$_3$): 7.17 (d, J=8.6 Hz, 2H), 6.82 (d, J=8.6 Hz, 2H), 4.25 (m, 1H), 3.64 (m, 1H), 3.42 (s, 1H), 3.40 (s, 2H), 2.80–2.69 (m, 5H), 2.36 (m, 2H), 2.08 (m, 2H), 2.02–1.94 (m, 2H), 1.87–1.74 (m, 2H), 1.55 (m, 2H), 1.04 (d, J=6.6 Hz, 6H).

Example 68

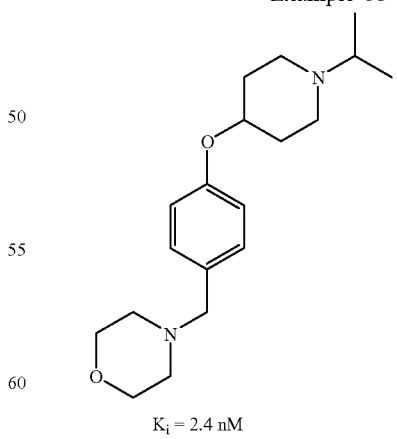

$K_i = 2.4$ nM

4-[4-(1-Isopropyl-piperidin-4-yloxy)-benzyl]-morpholine

A solution of the product of Example 2 (360 mg), morpholine (0.13 mL), and acetic acid (0.09 mL) in DCM (5 mL) was treated with sodium triacetoxyborohydride (450 mg). After 16 h, the resulting mixture was treated with 10% sodium hydroxide (10 mL), and the mixture was extracted with DCM (3×20 mL). The combined organic phases were dried (sodium sulfate) and evaporated. Chromatography of the residue (1–7% 2M methanolic ammonia/DCM) gave the title compound as a clear oil (366 mg). $^1$H NMR (400 MHz, CDCl$_3$): 7.20 (d, J=8.6 Hz, 2H), 6.82 (d, J=8.6 Hz, 2H), 4.27 (m, 1H), 3.69 (m, 4H), 3.42 (s, 2H), 2.82–2.70 (m, 3H), 2.41 (m, 4H), 2.36 (m, 2H), 2.04–1.96 (m, 2H), 1.84–1.75 (m, 2H), 1.05 (d, J=6.6 Hz, 6H).

Example 69

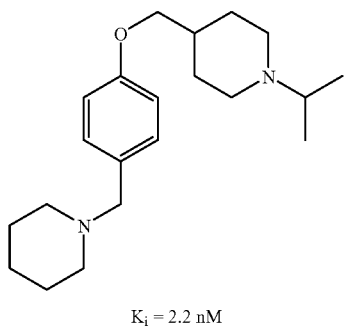

$K_i$ = 2.2 nM

1-[4-(1-Isopropyl-piperidin-4-ylmethoxy)-benzyl]-piperidine

A solution of 4-hydroxymethylpiperidine (23.1 g), acetone (40 mL), acetic acid (12 mL) and sodium triacetoxyborohydride (62 g) in DCM (3 mL) was stirred under nitrogen overnight at room temperature. The reaction mixture was basified with 10% aqueous sodium hydroxide to a pH of 12–13. The resulting mixture was extracted with dichloromethane (3×150 mL). The combined extracts were dried (sodium sulfate), filtered and evaporated, yielding an oil (31.47 g). A portion of this oil (595 mg) was added to a suspension of sodium hydride (151 mg) in dimethyl formamide (4 mL) under nitrogen. After 30 min, a solution of 4-cyanochlorobenzene (521 mg) in dimethyl formamide (2 mL) was added. The reaction mixture was heated to 65–68° C. for 18 hours, cooled to RT, and poured into water (200 mL). The resulting mixture was extracted with ethyl acetate (3×30 mL). The combined extracts were washed with water, brine and water and then dried (sodium sulfate). The residue was chromatographed (5% 2 M methanolic ammonia/DCM). This product (230 mg) was then dissolved in toluene, cooled to 0° C., and treated with di-isobutyl aluminum hydride (2.2 mL of a 1 M solution in hexane). The reaction mixture was warmed to RT, stirred for 16 hours, and quenched with ethyl acetate (1 mL). Sodium hydroxide (20 mL of a 1 M aqueous solution) was added, and the resulting mixture was stirred for five minutes and then extracted with DCM (2×30 mL). The combined organic phases were evaporated, and the residue was chromatographed (5% 2 M methanolic ammonia/DCM). A suspension of this product (100 mg), piperidine (38 µL), acetic acid (22 µL) and sodium triacetoxyborohydride (122 mg) in DCE (3 mL) was stirred overnight. The reaction mixture was quenched with 1 N aqueous sodium hydroxide (1 mL) and extracted with DCM (3×20 mL). The combined extracts were evaporated to dryness. Chromatography of the residue (5% 2 M methanolic ammonia/DCM) yielded the title compound (13 mg). $^1$H NMR (400 MHz, CDCl$_3$): 7.20 (d, J=8.59 Hz, 2 H), 6.83 (d, J=8.6 Hz, 2 H), 3.78 (d, J=6.3 Hz, 2 H), 2.95 (d, J=12Hz, 2 H), 2.75 (m, 1 H), 2.37 (brs, 4 H), 2.19 (m, 3 H), 1.83 (m, 4 H), 1.57 (m, 4 H), 1.42 (m, 4 H), 1.08 (d, J=6.6 Hz, 6 H).

Example 70

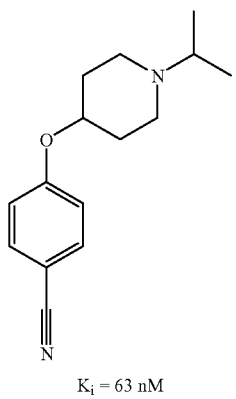

$K_i$ = 63 nM 4-(1-Isopropyl-piperidin-4-yloxy)-benzonitrile

A solution of the product of Example 3 (10.74 g) and 4-Chloro-benzonitrile (11.45 g) in DMF (100 mL) was treated with NaH (60%, 3.7 g). The resulting dark mixture was then heated to 65° C. for 16 h, and allowed to cool to RT. The mixture was poured into water (1.5 L) and extracted with ether (3×400 mL). The combined organic phases were dried (sodium sulfate) and evaporated which gave the title compound as a light brown solid (16.6 g). $^1$H NMR (400 MHz, CDCl$_3$): 7.56 (d, J=8.6 Hz, 2H), 6.93 (d, J=8.6 Hz, 2H), 4.37 (m, 1H), 2.81–2.72 (m, 3H), 2.41 (m, 4H), 2.06–1.98 (m, 2H), 1.87–1.77 (m, 2H), 1.06 (d, J=6.6 Hz, 6H).

Example 71

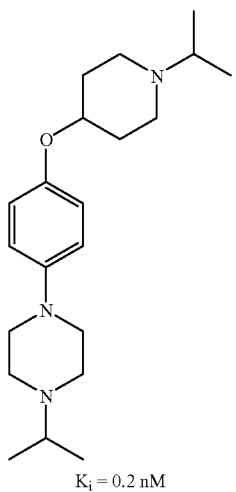

$K_i$ = 0.2 nM

1-Isopropyl-4-[4-(1-isopropyl-piperidin-4-yloxy)-phenyl]-piperazine

A solution of the product of Example 74 (0.061 mg), acetone (2 mL), and acetic acid (0.012 mL) in DCM (10 mL) was treated with sodium triacetoxyborohydride (59 mg). After 16 h, the resulting mixture was treated with 10% aqueous sodium hydroxide (5 mL). The aqueous phase was extracted with DCM (2×50 mL). The combined organic phases were washed with water (10 mL), brine (10 mL), dried (magnesium sulfate), and evaporated. Chromatography of the residue (4–10% 2M methanolic ammonia) gave the title compound as a colorless solid (40 mg). $^1$H NMR (400 MHz, CDCl$_3$): 6.90–6.83 (m, 4H), 4.19–4.15 (m, 1H), 3.11 (t, J=5.0 Hz, 4H), 2.81–2.67 (m, 8H), 2.38–2.33 (m, 2H), 2.02–1.95 (m, 2H), 1.82–1.74 (m, 2H), 1.09 (d, J=6.5 Hz, 6H), 1.05 (d, J=6.6 Hz, 6H).

Example 72

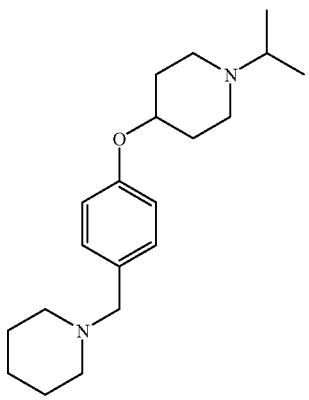

$K_i$ = 0.4 nM

1-[4-(1-Isopropyl-piperidin-4-yloxy)-benzyl]-piperidine

A suspension of the product of Example 3 (129 mg), the product of Example 1 (172 mg), and polymer-supported triphenylphosphine (600 mg) in DCM (5 mL) was treated with di-tert-butyl azodicarboxylate (311 mg). The resulting mixture was shaken for 16 h and filtered through a pad of celite. The pad was washed with DCM (3×1 mL) and the combined filtrates were chromatographed (1–6% 2 M methanolic ammonia/DCM), giving the title compound as a colorless oil (75 mg). $^1$H NMR (400 MHz, CDCl$_3$): 7.19 (d, J=8.5 Hz, 2H), 6.84 (d, J=8.6 Hz, 2H), 4.29–4.25 (m, 1H), 3.40 (s, 2H), 2.82–2.71 (m, 3H), 2.41–2.35 (m, 6H), 2.40–2.26 (m, 6H), 2.03–1.99 (m, 2H), 1.85–1.77 (m, 2H), 1.59–1.53 (m, 4H), 1.43–1.38 (m, 2H), 1.06 (d, J=6.6 Hz, 6H), Example 73

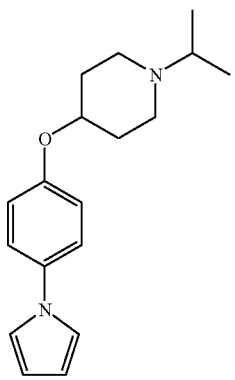

$K_i$ = 10 nM

1-Isopropyl-4-(4-pyrrol-1-yl-phenoxy)-piperidine

A suspension of the product of Example 3 (129 mg), 4-(1H-pyrrol)-1-yl)phenol (143 mg), and polymer-supported triphenylphosphine (600 mg) in DCM (5 mL) was treated with di-tert-butyl azodicarboxylate (311 mg). The resulting mixture was shaken for 16 h and filtered through a pad of celite. The pad was washed with DCM (3×1 mL) and the combined filtrates were chromatographed (1–6% 2 M methanolic ammonia/DCM), giving the title compound as a light yellow oil (92 mg). $^1$H NMR (400 MHz, CDCl$_3$): 7.27 (d, J=8.9 Hz, 2H), 6.99–6.98 (m, 2H), 6.93 (d, J=8.9 Hz, 2H), 6.31–6.30 (m, 2H), 4.30–4.26 (m, 1H), 2.82–2.71 (m, 3H), 2.42–2.36 (m, 2H), 2.04–2.00 (m, 2H), 1.86–1.78 (m, 2H), 1.06 (d, J=6.6 Hz, 6H).

Example 74

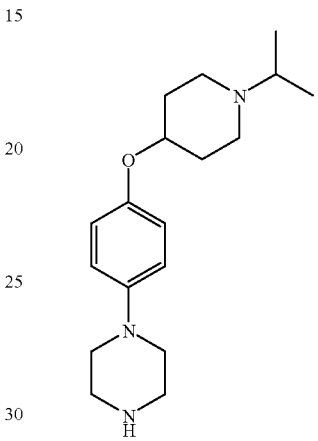

$K_i$ = 0.7 nM

1-[4-(1-Isopropyl-piperidin-4-yloxy)-phenyl]-piperazine

A solution of 1-(4-hydroxyphenyl)-piperazine (12.0 g) in THF (50 mL) was treated with di-tert butyl dicarbonate (72 mL of a 1 M solution in THF). After 10 min, saturated aqueous sodium bicarbonate was added. After 16 h, the resulting mixture was extracted with ethyl acetate (1.5 L). The organic phase was washed with water (2×200 mL), brine (200 mL), and then dried (magnesium sulfate) and evaporated. The resulting brown oil was triturated with hexane, giving a brown solid (16.3 g). A suspension of this brown solid (501 mg), the product of Example 66 (258 mg), and polymer-supported triphenylphosphine (1.2 g) in DCM (12 mL) was treated with di-tert-butyl azodicarboxylate (622 mg). The resulting mixture was shaken for 16 h and filtered through a pad of celite. The pad was washed with DCM (3×2 mL) and the combined filtrates were chromatographed (1–6% 2 M methanolic ammonia/DCM) giving the title compound as a brown oil (275 mg). A solution of this brown oil (259 mg) in dioxane (5 mL) was treated with hydrogen chloride (5 mL of a 4 N solution in dioxane). After 16 h solvent was evaporated and the residue was treated with 10% aqueous sodium hydroxide (20 mL) and extracted with DCM (2×100 mL). The combined organic phases were washed with water (50 mL), brine (50 mL), and dried (magnesium sulfate) and evaporated. Chromatography of the residue (6–20% 2 M methanolic ammonia/DCM) gave the title compound as a colorless oil (61 mg). $^1$H NMR (400 MHz, CDCl$_3$): 6.89–6.83 (m, 4H), 4.21–4.15 (m, 1H), 3.03 (s, 8H), 2.82–2.72 (m, 3H), 2.41–2.35 (m, 2H), 2.03–1.97 (m, 2H), 1.83–1.75 (m, 2H), 1.06 (d, J=6.6 Hz, 6H).

Example 75

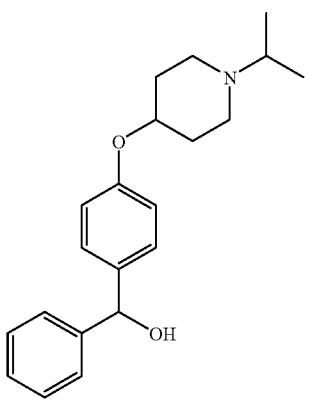

$K_i$ = 9.5 nM

[4-(1-Isopropyl-piperidin-4-yloxy)-phenyl]-phenyl-methanol

A solution of the product of Example 75 (65 mg) in ethanol (10 mL) was treated with sodium borohydride (1 g). After 16 h, the resulting mixture was treated with saturated aqueous sodium bicarbonate (20 mL), and extracted with DCM (2×50 mL). The combined organic phases were dried (magnesium sulfate) and evaporated. Chromatography of the residue (1–10% 2 M methanolic ammonia/DCM) gave the title compound as a colorless oil (52 mg). $^1$H NMR (400 MHz, CDCl$_3$): 7.38–7.21 (m, 7H), 6.86–6.82 (m, 2H), 5.76 (s, 1H), 4.27–4.23 (m, 1H), 2.77–2.68 (m, 3H), 2.39–2.34 (m, 2H), 2.01–1.96 (m, 2H), 1.81–1.72 (m, 2H), 1.04 (d, J=6.6 Hz, 6H).

Example 76

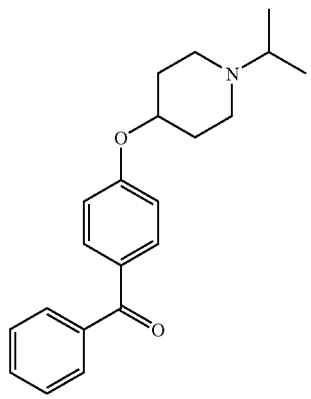

$K_i$ = 2.9 nM

[4-(1-Isopropyl-piperidin-4-yloxy)-phenyl]-phenyl-methanone

A suspension of the product of Example 66 (258 mg), 4-hydroxybenzophenone (357 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a colorless oil (151 mg). $^1$H NMR (400 MHz, CDCl$_3$): 7.81 (d, J=8.9 Hz, 2H), 7.76–7.74 (m, 2H), 7.59–7.54 (m, 1H), 6.96 (d, J=8.8 Hz, 2H), 4.46–4.40 (m, 1H), 2.83–2.73 (m, 3H), 2.46–2.40 (m, 2H), 2.08–2.03 (m, 2H), 1.90–1.82 (m, 2H), 1.07 (d, J=6.5 Hz, 6H).

Example 77

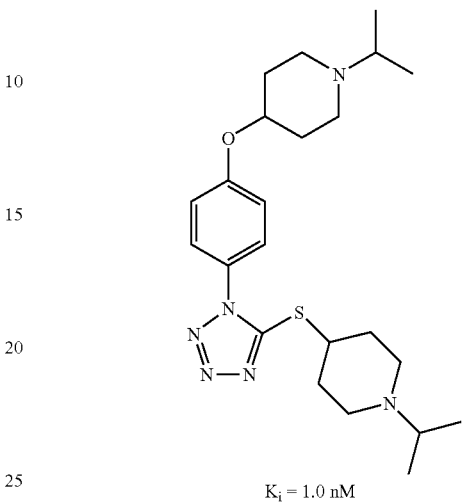

$K_i$ = 1.0 nM

N-Isopropyl-4-{4-[5-(1-isopropyl-piperidin-4-ylsulfanyl)-tetrazol-1-yl]-phenoxy}-piperidine A suspension of the product of Example 66 (258 mg), 1-(4-hydroxyphenyl)-1H-tetrazole-5-thiol (175 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a colorless oil (54 mg). $^1$H NMR (400 MHz, CDCl$_3$): 7.44–7.41 (m, 2H), 7.05–7.02 (m, 2H), 4.39–4.36 (m, 1H), 3.97–3.92(m, 1H), 2.86–2.70 (m, 6H), 2.46–2.40 (m, 4H), 2.38–2.24 (m, 2H), 2.07–2.03 (m, 2H), 1.89–1.74 (m, 4H), 1.07 (d, J=6.5 Hz, 6H), 1.04 (d, J=6.6 Hz, 6H).

Example 78

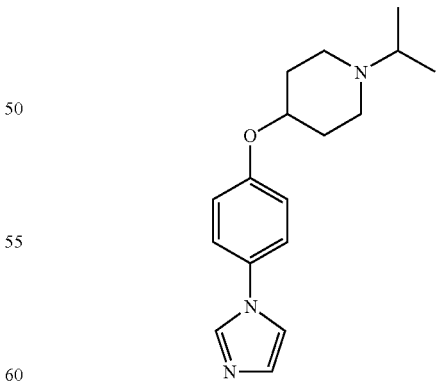

$K_i$ = 6.3 nM 4-(4-Imidazol-1-yl-phenoxy)-1-isopropyl-piperidine

A suspension of the product of Example 66 (258 mg), 4-(imidazol-1-yl)phenol (144 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a colorless oil (67 mg). $^1$H NMR (400 MHz, CDCl$_3$): 7.76 (s, 1H), 7.30–7.26 (m, 2H), 7.21–7.18 (m, 2H), 7.01–6.97 (m, 2H), 4.36–4.30 (m, 1H), 2.85–2.75 (m, 3H), 2.44–2.39 (m, 2H), 2.07–2.01 (m, 2H), 1.88–1.80 (m, 2H), 1.07 (d, J=6.6 Hz, 6H).

Example 79

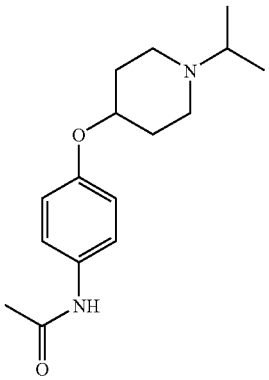

$K_i = 17$ nM

N-[4-(1-Isopropyl-piperidin-4-yloxy)-phenyl]-acetamide

A suspension of the product of Example 66 (258 mg), acetaminophen (136 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a colorless oil (82 mg). $^1$H NMR (400 MHz, CDCl$_3$): 8.14 (s, 1H), 7.39–7.35 (m, 2H), 6.84–6.80 (m, 2H), 4.24–4.18 (m, 1H), 2.80–2.72 (m, 3H), 2.39–2.33 (m, 2H), 2.10 (s, 3H), 2.00–1.95 (m, 2H), 1.81–1.73 (m, 2H), 1.05 (d, J=6.6 Hz, 6H).

Example 80

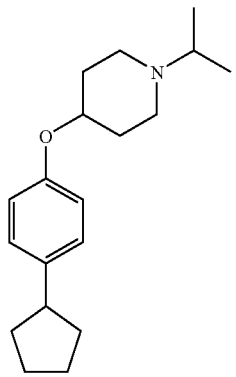

$K_i = 19$ nM 4-(4-Cyclopentyl-phenoxy)-1-isopropyl-piperidine

A suspension of the product of Example 66 (258 mg), 4-cyclopentylphenol (146 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a colorless oil (19 mg). $^1$H NMR (400 MHz, CDCl$_3$): 7.15–7.12 (m, 2H), 6.85–6.81 (m, 2H), 4.28–4.22 (m, 1H), 2.97–2.88 (m, 1H), 2.42–2.36 (m, 2H), 2.07–1.99 (m, 4H), 1.85–1.49 (m, 8H), 1.06 (d, J=6.6 Hz, 6H).

Example 81

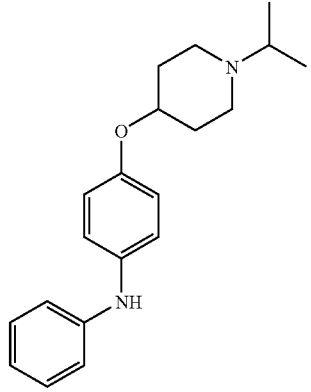

$K_i = 3.7$ nM

[4-(1-Isopropyl-piperidin-4-yloxy)-phenyl]-phenyl-amine

A suspension of the product of Example 66 (258 mg), 4-hydroxydiphenylamine (136 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a brown oil (25 mg). $^1$H NMR (400 MHz, CDCl$_3$): 7.23–7.19 (m, 2H), 7.06–7.03 (m, 2H), 6.93–6.91 (m, 2H), 6.88–6.81 (m, 3H), 4.26–4.20 (m, 1H), 2.84–2.74 (m, 3H), 2.44–2.38 (m, 2H), 2.06–2.00 (m, 2H), 1.07 (d, J=6.6 Hz, 6H).

Example 82

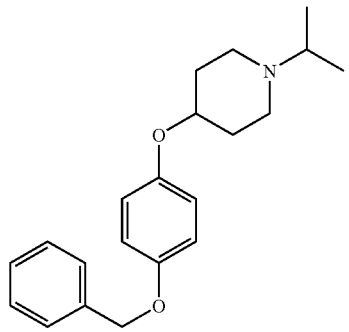

$K_i = 6$ nM 4-(4-Benzyloxy-phenoxy)-1-isopropyl-piperidine

A suspension of the product of Example 66 (258 mg), 4-(benzyloxy)phenol (180 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a light pink solid (102 mg). $^1$H NMR (400 MHz, CDCl$_3$): 7.43–7.28 (m, 5H), 6.91–6.82 (m, 4H), 5.00 (s, 2H), 4.18–4.13 (m, 1H), 2.81–2.69 (m, 3H), 2.38–2.32 (m, 2H), 2.01–1.95 (m, 2H), 1.82–1.74 (m, 2H), 1.05 (d, J=6.6 Hz, 6H).

Example 83

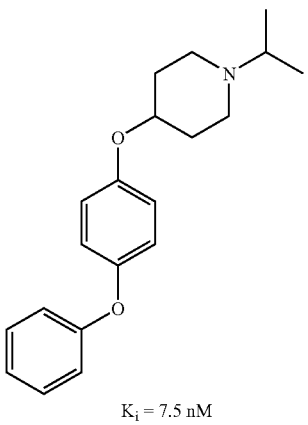

$K_i$ = 7.5 nM

1-Isopropyl-4-(4-phenoxy-phenoxy)-piperidine

A suspension of the product of Example 66 (258 mg), 4-phenoxyphenol (168 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a colorless oil (77 mg). $^1$H NMR (400 MHz, CDCl$_3$): 7.31–7.26 (m, 2H), 7.05–7.01 (m, 1H), 6.97–6.92 (m, 4H), 6.90–6.86 (m, 2H), 4.25–4.20 (m, 1H), 2.83–2.72 (m, 3H), 2.41–2.35 (m, 2H), 2.05–1.99 (m, 2H), 1.86–1.77 (m, 2H), 1.06 (d, J=6.6 Hz, 6H).

Example 84

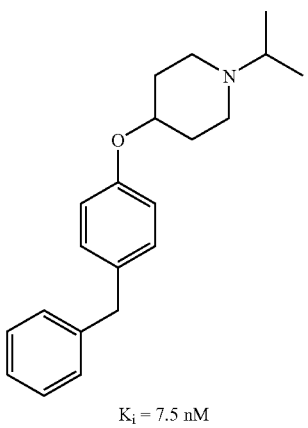

$K_i$ = 7.5 nM 4-(4-Benzyl-phenoxy)-1-isopropyl-piperidine

A suspension of the product of Example 66 (258 mg), 4-hydroxydiphenylmethane (166 mg), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a light yellow oil (108 mg). $^1$H NMR (400 MHz, CDCl$_3$): 7.30–7.26 (m, 2H), 7.20–7.16 (m, 3H), 7.09–7.06 (m, 2H), 6.84–6.81 (m, 2H), 4.27–4.21 (m, 1H), 3.91 (s, 2H), 2.81–2.67 (m, 3H), 2.40–2.34 (m, 2H), 2.02–1.92 (m, 2H), 1.83–1.75 (m, 2H), 1.05 (d, J=6.6 Hz, 6H).

Example 85

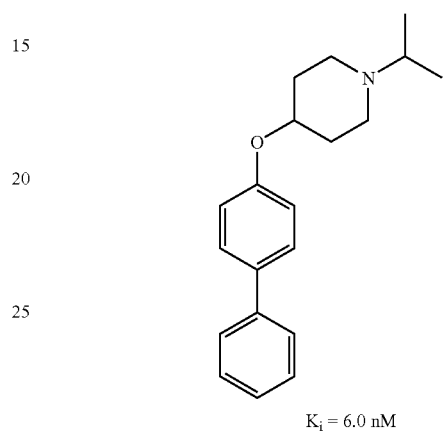

$K_i$ = 6.0 nM 4-(Biphenyl-4-yloxy)-1-isopropyl-piperidine

A suspension of the product of Example 66 (258 mg), acetone (0.039 mL), and polymer-supported triphenylphosphine (1.2 g) in DCM (6 mL) was treated with di-tert-butyl azodicarboxylate (622 mg). The resulting mixture was shaken for 16 h and filtered through a pad of celite. The pad was washed with DCM (3×1 mL) and the combined filtrates were chromatographed (1–6% 2 M methanolic ammonia/DCM) giving the title compound as a white solid (91 mg). $^1$H NMR (400 MHz, CDCl$_3$): 7.55–7.49 (m, 4H), 7.42–7.38 (m, 2H), 7.30–7.26 (m, 1H), 6.98–6.95 (m, 2H), 4.36–4.31 (m, 1H), 2.83–2.73 (m, 3H), 2.46–2.41 (m, 2H), 2.09–2.05 (m, 2H), 1.90–1.82 (m, 2H), 1.08 (d, J=6.6 Hz, 6H).

Example 86

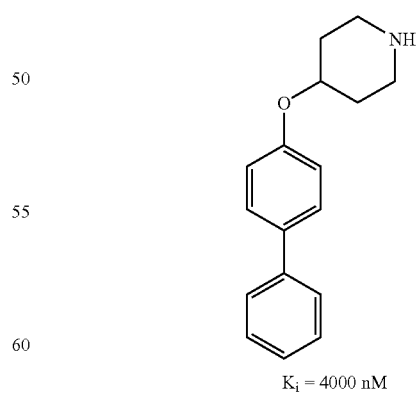

$K_i$ = 4000 nM 4-(Biphenyl-4-yloxy)-piperidine

A suspension of tert-butyl 4-hydroxy-1-piperidine carboxylate (497 mg), 4-phenylphenol (300 mg), and polymer-supported triphenylphosphine (1.2 g) in DCM (10 mL) was treated with di-tert-butyl azodicarboxylate (608 mg). The resulting mixture was shaken for 16 h, and filtered through a pad of celite. The pad was washed with DCM (3×5 mL) and the combined filtrates were evaporated. The residue was dissolved in dioxane (5 mL) and treated with hydrogen chloride (5 mL of a 4 N solution in dioxane). After 16 h, solvent was removed and the residue was treated with 10% aqueous sodium hydroxide (20 mL). The resulting mixture was extracted with DCM (2×500 mL), and the combined organic phases were dried (magnesium sulfate) and evaporated. Chromatography of the residue (1–6% 2M methanolic ammonia/DCM) gave the title compound as a white solid (107 mg). $^1$H NMR (400 MHz, CDCl$_3$): 7.56–7.49 (m, 4H), 7.42–7.39 (m, 2H), 7.31–7.27 (m, 1H), 6.99–6.96 (m, 2H), 4.43–4.37 (m, 1H), 3.18–3.13 (m, 3H), 2.77–2.70 (m, 2H), 2.07–2.01 (m, 2H), 1.73–1.64 (m, 2H).

Example 87

Biological Methods

In Vitro

Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% CO$_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165–2088). One microgram of supercoiled H$_3$ receptor cDNA was added to the cells and mixed. The voltage for the electroporation was set at 0.25 kV, the capacitance was set at 960 μF. After electroporation the cells were diluted into 10 mL complete media and plated onto four 10 cm dishes. Because of the variability in the efficiency of electroporation, four different concentrations of cells were plated. The ratios used were; 1:20, 1:10, 1:5, with the remainder of the cells being added to the fourth dish. The cells were allowed to recover for 24 hours before adding the selection media (complete media with 600 μg/mL G418). After 10 days dishes were analyzed for surviving colonies of cells. Dishes with well isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

[$^3$H]-N-methylhistamine Binding

Cell pellets from histamine H$_3$ receptor-expressing SK-N-MC cells were homogenized in 20 mM TrisHCl/0.5 mM EDTA. Supernatants from a 800 g spin were collected, recentrifuged at 30,000 g for 30 minutes. Pellets were re-homogenized in 50 mM Tris/5 mM EDTA (pH 7.4). Membranes were incubated with 0.8 nM [$^3$H]-N-methylhistamine plus/minus test compounds for 45 min at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 μM histamine. The pK$_i$ values were calculated based on a K$_d$ of 800 pM and a ligand concentration ([L]) of 800 pM according to the formula:

$K_i=(IC_{50})/(1+([L]/(K_d))$

In Vivo

Elucidation of Oral Absorption and Blood-brain Barrier Penetration Profiles of H$_3$ Receptor Antagonists in the Rat A rat in vivo system was used to determine the blood-brain barrier penetration profiles and kinetics of various H$_3$ receptor antagonists after single bolus oral administration.

Female Sprague Dawley Rats (~300 gram body weight) were housed in accordance with institutional standards and allowed to acclimate for at least 7 days prior to the study. Each H$_3$ antagonist was formulated in 0.5% hydroxypropylmethyl cellulose at a concentration of 1 mg/mL for oral dosing. The test compound was administered to each of eight animals as a single oral dose of 10 mL/kg (10 mg/kg). Remaining dosing solution was retained for analysis. Two animals from each original group of eight were euthanized via CO$_2$ asphyxiation at t=1, 6, 24, and 48 hours. After each animal was euthanized, 0.1 mL of its blood was sampled via cardiac puncture, and its brain was removed via dissection of the cranial bones and placed in a pre-weighed 50 mL conical tube on dry ice.

The blood was added to 0.3 mL of 6% trichloroacetic acid, and the acidified sample was vortexed and then centrifuged (5 minutes at 14,000 rpm in a microcentrifuge). The clear supernatant was retained for analysis. The frozen brain was weighed, homogenized in 6% trichloroacetic acid (3 mL/g wet weight of tissue), and then centrifuged. The clear supernatant was retained for analysis. The supernatants from the blood and brain samples were analyzed by liquid chromatography with mass spectral detection utilizing selective reaction monitoring (LC-MS/MS). The LC method used a Phenomonex Polar RP column (2×50 mm) and a linear solvent gradient of water and acetonitrile (both 1% in acetic acid).

Graphs of H$_3$ receptor antagonist concentration versus time for blood and brain were generated from the LC-MS/MS results. The mean residency time (MRT) of the H$_3$ receptor antagonist, in blood or in the brain, was calculated from the ratio of the area under the first moment curve (AUMC) to the area under the concentration time curve (AUC): AUMC/AUC. The Blood Brain Barrier index was calculated from the log of AUC$_{brain}$/AUC$_{blood}$.

F. Other Embodiments

The features and advantages of the invention will be apparent to one of ordinary skill in view of the discussion, examples, embodiments, and claims relating to the invention. The invention also contemplates variations and adaptations, based on the disclosure herein concerning the key features and advantages of the invention, and within the abilities of one of ordinary skill.

What is claimed is:

1. A compound of formula (I):

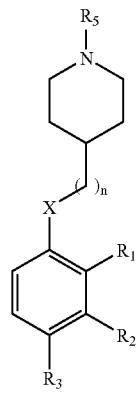

wherein X is O;

n is an integer from 0 to 3;

$R_5$ is $C_{1-10}$alkyl, $C_{3-8}$alkenyl, $C_{3-8}$cycloalkyl, $(C_{3-8}$cycloalkyl$)$ $C_{1-6}$alkyl, (phenyl)$C_{1-6}$alkyl, (phenyl)$C_{3-8}$alkenyl, or $(C_{1-8}$alkylcarbonyl$)C_{1-8}$alkyl;

one of $R_1$, $R_2$, and $R_3$ is W or G, wherein one of the remaining two is selected from H and halogen, and the third being hydrogen;

W is piperazinyl or morpholinyl;

G is piperazinylmethyl or morpholinylmethyl;

wherein each of the above alkyl, alkylene, alkenyl, alkenylene, alkynyl, alkynylene, heterocyclyl, cycloalkyl, and aryl groups may each be independently and optionally substituted with between 1 and 3 substituents selected from halo, amino, nitro, hydroxyl, and $C_{1-3}$alkyl;

or a pharmaceutically acceptable salt, ester, or amide thereof.

2. A compound of claim 1, wherein $R_5$ is $C_{1-5}$alkyl, $C_{3-4}$alkenyl, $C_{3-6}$cycloalkyl, $(C_{3-6}$cycloalkyl$)C_1$alkylene, (phenyl)$C_{1-3}$alkylene, or (phenyl)$C_{3-4}$alkenylene.

3. A compound of claim 2, wherein $R_5$ is branched $C_{3-5}$alkyl, $C_{3-6}$cycloalkyl, and $(C_{3-6}$cycloalkyl$)C_1$alkylene.

4. A compound of claim 1, wherein one of $R_2$ and $R_3$ is W.

5. A compound of claim 4, wherein $R_2$ is W.

6. A compound of claim 4, wherein $R_3$ is W.

7. A compound of claim 1, wherein W is a substituted or unsubstituted N-morpholinyl.

8. A compound of claim 1, wherein $R_5$ is $C_{1-5}$alkyl, $C_{3-4}$alkenyl, $C_{3-6}$cycloalkyl, $(C_{3-6}$cycloalkyl$)$ $C_1$alkylene, (phenyl)$C_{1-3}$alkylene, or (phenyl)$C_{3-4}$alkenylene.

9. A compound of claim 1, wherein n is 0 or 1.

10. A compound of claim 9, wherein n is 0.

11. A compound of claim 1, wherein $R_5$ is $C_{1-5}$alkyl, $C_{3-4}$alkenyl, $C_{3-6}$cycloalkyl, $(C_{3-6}$cycloalkyl$)C_1$alkylene, (phenyl)$C_{1-3}$ alkylene, or (phenyl)$C_{3-4}$alkenylene.

12. A compound of claim 1, wherein one of $R_2$ and $R_3$ is W.

13. A compound of claim 9, wherein $R_5$ is branched $C_{3-5}$alkyl.

14. A compound of claim 9, wherein $R_5$ is isopropyl or cyclopentyl.

15. A compound of claim 1, selected from 1-Isopropyl-4-[4-(1-isopropyl-piperidin-4-yloxy)-phenyl]-piperazine, 1-[4-(1-Isopropyl-piperidin-4-yloxy)-phenyl]-piperazine, and 1-[4-(1-Isopropyl-piperidin-4-yloxy)-phenyl]-piperazine.

16. A pharmaceutical composition, comprising a compound of claim 1 and a pharmaceutically acceptable carrier.

17. A compound of claim 1, selected from 4-[4-(1-sec-butyl-piperidin-4-yloxy)-benzyl]-morpholine, 1-[4-(1-Isopropyl-piperidin-4-yloxy)-benzyl]-4-methyl-piperazine, 4-[4-(1-sec-butyl-piperidin-4-yloxy)-benzyl]-morpholine, 1-[4-(1-isopropyl-piperidin-4-yloxy)-benzyl]-4-phenyl-piperazine, 1-benzyl-4-[4-(1-isopropyl-piperidin-4-yloxy)-benzyl]-piperazine, 4-[4-(1-isopropyl-piperidin-4-yloxy)-benzyl]-morpholine, 4-[4-(1-cyclohexyl-piperidin-4-yloxy)-benzyl]-morpholine, 4-[4-(1-isobutyl-piperidin-4-yloxy)-benzyl]-morpholine, 4-[4-(1-propyl-piperidin-4-yloxy)-benzyl]-morpholine; and 4-[4-(1-cyclopentyl-piperidin-4-yloxy)-benzyl]- morpholine.

* * * * *